US010472624B2

(12) United States Patent
Takahashi et al.

(10) Patent No.: US 10,472,624 B2
(45) Date of Patent: Nov. 12, 2019

(54) MORPHOLINO OLIGONUCLEOTIDE MANUFACTURING METHOD

(71) Applicant: AJINOMOTO CO., INC., Tokyo (JP)

(72) Inventors: Daisuke Takahashi, Yokkaichi (JP); Takayoshi Torii, Yokkaichi (JP)

(73) Assignee: AJINOMOTO CO., INC., Tokyo (JP)

( * ) Notice: Subject to any disclaimer, the term of this patent is extended or adjusted under 35 U.S.C. 154(b) by 23 days.

(21) Appl. No.: 15/487,720

(22) Filed: Apr. 14, 2017

(65) Prior Publication Data

US 2017/0218361 A1 Aug. 3, 2017

Related U.S. Application Data

(63) Continuation of application No. PCT/JP2015/078960, filed on Oct. 13, 2015.

(30) Foreign Application Priority Data

Oct. 14, 2014 (JP) .................................. 2014-210046

(51) Int. Cl.
| | |
|---|---|
| *C07F 9/6533* | (2006.01) |
| *C07F 9/6558* | (2006.01) |
| *C12N 15/11* | (2006.01) |
| *C12N 15/09* | (2006.01) |
| *C12N 15/113* | (2010.01) |
| *A61K 31/7052* | (2006.01) |

(52) U.S. Cl.
CPC .......... *C12N 15/111* (2013.01); *C07F 9/6533* (2013.01); *C07F 9/6558* (2013.01); *C12N 15/09* (2013.01); *C12N 15/113* (2013.01); *A61K 31/7052* (2013.01); *C12N 2310/11* (2013.01); *C12N 2310/3233* (2013.01); *Y02P 20/55* (2015.11)

(58) Field of Classification Search
CPC .............................. C07F 9/6533; C07F 9/6558
See application file for complete search history.

(56) References Cited

U.S. PATENT DOCUMENTS

| | | | |
|---|---|---|---|
| 5,185,444 A | 2/1993 | Summerton et al. | |
| 5,596,086 A | 1/1997 | Matteucci et al. | |
| 7,790,694 B2 | 9/2010 | Geller et al. | |
| 8,067,571 B2 | 11/2011 | Weller et al. | |
| 8,076,476 B2 | 12/2011 | Reeves et al. | |
| 8,299,206 B2 | 10/2012 | Fox et al. | |
| 8,536,147 B2 | 9/2013 | Weller et al. | |
| 8,785,407 B2 | 7/2014 | Stein et al. | |
| 8,969,551 B2 | 3/2015 | Ueda | |
| 9,249,243 B2 | 2/2016 | Weller et al. | |
| 9,278,987 B2 | 3/2016 | Hanson et al. | |
| 9,499,583 B2 | 11/2016 | Weller et al. | |
| 9,512,424 B2 | 12/2016 | Watanabe et al. | |
| 9,790,497 B2 * | 10/2017 | Torii .................... | C07D 413/04 |
| 2004/0033973 A1 | 2/2004 | Manoharan et al. | |
| 2007/0135333 A1 | 6/2007 | Geller et al. | |
| 2007/0265214 A1 | 11/2007 | Stein et al. | |
| 2008/0194463 A1 | 8/2008 | Weller et al. | |
| 2009/0131624 A1 | 5/2009 | Reeves et al. | |
| 2009/0131632 A1 | 5/2009 | Fox et al. | |
| 2010/0099159 A1 | 4/2010 | Deiters | |
| 2010/0234280 A1 | 9/2010 | Geller et al. | |
| 2010/0234281 A1 | 9/2010 | Weller et al. | |
| 2012/0296087 A1 | 11/2012 | Sinha et al. | |
| 2013/0197220 A1 | 8/2013 | Ueda | |
| 2013/0267697 A1 | 10/2013 | Hirai et al. | |
| 2014/0213737 A1 | 7/2014 | Weller et al. | |
| 2014/0330006 A1 | 11/2014 | Hanson et al. | |
| 2014/0343266 A1 | 11/2014 | Watanabe et al. | |
| 2016/0076033 A1 | 3/2016 | Torii et al. | |
| 2016/0251398 A1 | 9/2016 | Weller et al. | |
| 2016/0376587 A1 | 12/2016 | Hanson et al. | |
| 2017/0067052 A1 | 3/2017 | Watanabe et al. | |

FOREIGN PATENT DOCUMENTS

| | | |
|---|---|---|
| CN | 103476784 A | 12/2013 |
| JP | 5-504563 A | 7/1993 |
| JP | 2010-505741 A | 2/2010 |
| JP | 2011-503184 A | 1/2011 |
| WO | WO 91/09033 A1 | 6/1991 |
| WO | WO 92/05186 A1 | 4/1992 |
| WO | WO 2008/008113 A1 | 1/2008 |
| WO | WO 2009/064471 A1 | 5/2009 |
| WO | WO 2011/018798 A2 | 2/2011 |
| WO | WO 2012/043730 A1 | 4/2012 |
| WO | WO 2013/074834 A1 | 5/2013 |
| WO | WO 2013/100190 A1 | 7/2013 |
| WO | WO 2013/122236 A1 | 8/2013 |
| WO | WO 2014/189142 A1 | 11/2014 |

OTHER PUBLICATIONS

Osamu Sakatsume, et al., "Synthesis of Oligoribonucleotides Bearing Morpholino-Nucleosides with Carbamate Internucleoside Linkages at the 3'-Terminus", Chemistry Letters, XP009154057, 1993, pp. 201-204.

Eugene P. Stirchak, et al., "Uncharged stereoregular nucleic acid analogs: 2. Morpholino nucleoside oligomers with carbamate internucleoside linkages", Nucleic Acids Research, vol. 17, No. 15, XP001084030, 1989, pp. 6129-6141.

Bappaditya Nandi, et al., "Synthesis of Nucleobase-Functionalized Morpholino-Modified Nucleoside Monomers Through Palladium-Catalyzed Cross-Coupling Reactions", European Journal of Organic Chemistry, 2013, 55(5), pp. 1271-1286.

James Summerton et al., "Morpholino Antisense Oligomers: Design, Preparation, and Properties", Antisense & Nucleic Acid Drug Development, 1997, vol. 7, pp. 187-195.

Taro Harakawa et al., "Development of an efficient method for phosphorodiamidate bond formation by using inorganic salts" Bioorganic & Medicinal Chemistry Letters, 2012, vol. 22, pp. 1445-1447.

* cited by examiner

*Primary Examiner* — Joseph R Kosack

(74) *Attorney, Agent, or Firm* — Oblon, McClelland, Maier & Neustadt, L.L.P.

(57) ABSTRACT

Morpholino oligonucleotides can be produced efficiently in a high yield by a liquid-phase synthesis method, which includes subjecting a reaction mixture of a condensation reaction to an extraction operation and separating the morpholino oligonucleotide as a resultant product to the organic layer side.

7 Claims, No Drawings

MORPHOLINO OLIGONUCLEOTIDE MANUFACTURING METHOD

CROSS REFERENCES TO RELATED APPLICATIONS

This application is a continuation of International Patent Application No. PCT/JP2015/078960, filed on Oct. 13, 2015, and claims priority to Japanese Patent Application No. 2014-210046, filed on Oct. 14, 2014, both of which are incorporated herein by reference in their entireties.

BACKGROUND OF THE INVENTION

Field of the Invention

The present invention relates to methods for producing a morpholino oligonucleotide. The present invention also relates to morpholino nucleotides used as a starting material in such a production method.

Discussion of the Background

Morpholino oligonucleotides are compounds attracting attention for their use as antisense oligonucleotides, since they show high affinity for DNA and RNA, resistance to various nucleases, stability in vivo, and low toxicity (see Summerton, J. et al., Antisense and Nucleic Acid Drug Development, 1997, Vol. 7, p. 187, which is incorporated herein by reference in its entirety).

As a production method of morpholino oligonucleotides, a solid-phase synthesis and a liquid-phase synthesis have been reported (see Harakawa et al., Bioorganic & Medicinal Chemistry Letters, 2012, Vol. 22, p. 1445-1447; WO 91/09033; WO 2008/008113; US 2009/0131632 A1; WO 2009/064471; and WO 2012/043730, all of which are incorporated herein by reference in their entireties).

Solid-phase synthesis is advantageous from the aspect of speed since it enables automatic synthesis. On the other hand, it is not suitable for industrial large scale synthesis since scaling-up is limited due to facility restriction, and low reactivity requires use of an excess monomer to be the reagent in a nucleotide elongation reaction. Also, it is associated with defects in that confirmation of the progress status of the reaction in an intermediate stage, analysis of intermediate structure and the like are difficult.

On the other hand, liquid-phase synthesis has problems of solubility, complexity of work-up and the like, and a large-scale and rapid synthesis of a morpholino oligonucleotide having a chain length utilizable as an antisense pharmaceutical product has been difficult.

Thus, there remains a need for improved methods for producing a morpholino oligonucleotide.

SUMMARY OF THE INVENTION

Accordingly, it is one object of the present invention to provide novel methods of producing a morpholino oligonucleotide.

It is another object of the present invention to provide novel methods of producing a morpholino oligonucleotide efficiently and in a high yield by a liquid-phase method.

It is another object of the present invention to provide novel morpholino nucleotides which are useful as starting materials in such a method.

These and other objects, which will become apparent during the following detailed description, have been achieved by the inventors' noting that, in the process of manufacturing morpholino oligonucleotide by a condensation reaction in the liquid phase, an isolation method of the objective compound by precipitation after deprotection reaction and condensation reaction requires complicated operation and enormous operation time, and their discovery that the object compound can be efficiently isolated by a method including work-up by an extraction operation instead of precipitation and removal of impurities into the aqueous layer side. They have further found that an elongation reaction of morpholino oligonucleotide can be performed in a single reaction container and so-called one-pot synthesis is possible by combining work-up by an extraction operation after deprotection, and work-up by an extraction operation after condensation reaction.

The present inventors also took note of the facts that, in the process of manufacturing morpholino oligonucleotide by a condensation reaction in the liquid phase, since a starting material, a morpholino nucleoside monomer, and remaining after condensation reaction is involved in the reaction in the next step, causes double addition and produces by-products, as the chain length becomes longer, purification becomes more difficult and elongation of morpholino oligonucleotide also becomes difficult, and found that impurities derived from the remaining starting material monomer can be efficiently removed to the aqueous layer side by an extraction operation by employing an extraction operation as work-up after condensation reaction, and by, for example, treating the system with a particular compound (quenching agent).

The present inventors also took note of the facts that, in the process of manufacturing morpholino oligonucleotide by a condensation reaction in the liquid phase, a protecting group-derived compound resulting from removal of a protecting group such as a trityl group and the like, which protects nitrogen of the morpholine ring before the condensation reaction, is involved in the reaction in the next condensation step and produces by-products, thereby also making it difficult to produce long-chain morpholino oligonucleotide in the liquid-phase synthesis, and found that impurities derived from the protecting group such as trityl group and the like can be efficiently removed to the aqueous layer side by an extraction operation by employing an extraction operation as work-up after deprotection and by, for example, treating the system with a particular compound (cation scavenger).

The present inventors have also found that, in the process of manufacturing morpholino oligonucleotide by a condensation reaction in the liquid phase, the aforementioned condensation reaction and deprotection reaction proceed preferably, the solubility of morpholino nucleotide in non-polar solvents and phase separating ability are improved when impurities are eliminated into the aqueous layer side by an extraction operation, impurities can be efficiently removed to the aqueous layer side by an extraction operation, and morpholino oligonucleotide can be elongation synthesized more efficiently, by protecting the 5'-terminus and/or a nucleic acid base with a protecting group having an alkyl group having not less than 10 and not more than 300 carbon atoms and/or an alkenyl group having not less than 10 and not more than 300 carbon atoms (hereinafter to be also referred to as "anchor") (hereinafter to be also referred to as "anchoring").

The present inventors have also found that, in the process of manufacturing morpholino oligonucleotide by a condensation reaction in the liquid phase, the aforementioned condensation reaction and deprotection reaction proceed preferably, the solubility of morpholino nucleotide in non-polar solvents and phase separating ability are improved when impurities are eliminated into the aqueous layer side by an extraction operation, and impurities can be efficiently removed to the aqueous layer side by an extraction operation, by using a morpholino nucleoside monomer wherein the nucleic acid base is protected by a protecting group having an alkyl group having not less than 10 and not more than 300 carbon atoms and/or an alkenyl group having not less than 10 and not more than 300 carbon atoms.

The present inventors also took note of the facts that, in the process of manufacturing morpholino oligonucleotide by a condensation reaction in the liquid phase, the aforementioned condensation reaction and deprotection reaction proceed preferably, the solubility of morpholino nucleotide in non-polar solvents and phase separating ability are improved when impurities are eliminated into the aqueous layer side by an extraction operation, impurities can be efficiently removed to the aqueous layer side by an extraction operation, and morpholino oligonucleotide can be elongation synthesized more efficiently, by employing, when a protecting group having an alkyl group having not less than 10 and not more than 300 carbon atoms and/or an alkenyl group having not less than 10 and not more than 300 carbon atoms is used as a protecting group as mentioned above, a protecting group having a branched chain alkyl group having not less than 10 and not more than 300 carbon atoms and/or a branched chain alkenyl group having not less than 10 and not more than 300 carbon atoms.

The present inventors have found that morpholino oligonucleotides can be produced efficiently and in a high yield by a liquid-phase method by using these methods, and completed the present invention.

That is, the present invention provides the following:

(1) A method of producing an n+p-mer morpholino oligonucleotide, comprising a step of condensing a p-mer morpholino oligonucleotide (p is any integer of one or more), wherein a 5'-hydroxy group is activated phosphoramidated, and a morpholine ring nitrogen atom is protected by a temporary protecting group removable under acidic conditions, with an n-mer morpholino oligonucleotide (n is any integer of one or more) wherein 5'-terminus and/or a nucleic acid base are/is each independently protected by a protecting group having an alkyl group having not less than 10 and not more than 300 carbon atoms and/or an alkenyl group having not less than 10 and not more than 300 carbon atoms or a protecting group removable under conditions different from those for the aforementioned temporary protecting group of the morpholine ring nitrogen atom, and the morpholine ring nitrogen atom is not protected, by a phosphoramidate bond or phosphorodiamidate bond via the morpholine ring nitrogen atom, and subjecting the obtained reaction mixture to an extraction operation to separate the n+p-mer morpholino oligonucleotide as a resultant product to the organic layer side (hereinafter to be referred to as "step (2)").

(2) The production method of (1), wherein at least one of the 5'-terminus and the nucleic acid base of the n-mer morpholino oligonucleotide, and the nucleic acid base of the p-mer morpholino oligonucleotide is protected by a protecting group having a branched chain alkyl group having not less than 10 and not more than 300 carbon atoms and/or a branched chain alkenyl group having not less than 10 and not more than 300 carbon atoms.

(3) The production method of (1), wherein the 5'-terminus of the n-mer morpholino oligonucleotide is protected by a protecting group having a branched chain alkyl group having not less than 10 and not more than 300 carbon atoms and/or a branched chain alkenyl group having not less than 10 and not more than 300 carbon atoms.

(4) The production method of (1), wherein the nucleic acid bases of the p-mer morpholino oligonucleotide are each independently protected by a protecting group having an alkyl group having not less than 10 and not more than 300 carbon atoms and/or an alkenyl group having not less than 10 and not more than 300 carbon atoms or a protecting group removable under conditions different from those for the aforementioned protecting group of the morpholine ring nitrogen atom.

(5) The production method of (1), wherein the reaction mixture is treated with a quenching agent before the extraction operation.

(6) The production method of (5), wherein the quenching agent comprises a compound having a secondary amino group and a carboxy group, or a compound having a phosphono group.

(7) The production method of (5), wherein the quenching agent comprises a compound having one secondary amino group and one or two carboxy groups.

(8) The production method of (5), wherein the quenching agent is prolylglutamic acid.

(9) The production method of (5), wherein the quenching agent is prolylproline.

(10) The production method of (5), wherein the quenching agent comprises a compound having a phosphono group.

(11) The production method of (5), wherein the quenching agent is phenylphosphonic acid.

(12) The production method of any of (1) to (11), further comprising the following step; a step of removing, before the step described in the aforementioned [1] (step (2)) and in a non-polar solvent, the temporary protecting group of the morpholine ring nitrogen atom from the n-mer morpholino oligonucleotide wherein the morpholine ring nitrogen atom is protected by a temporary protecting group removable under acidic conditions, and 5'-terminus and/or the nucleic acid base are/is each independently protected by a protecting group having an alkyl group having not less than 10 and not more than 300 carbon atoms and/or an alkenyl group having not less than 10 and not more than 300 carbon atoms or a protecting group removable under conditions different from those for the aforementioned protecting group of the morpholine ring nitrogen atom, and subjecting the obtained reaction mixture to an extraction operation to separate the n-mer morpholino oligonucleotide as a resultant product to the organic layer side (hereinafter to be referred to as "step (1)").

(13) The production method of (12), wherein the temporary protecting group of the morpholine ring nitrogen atom is removed by reacting with an acid in the presence of a cation scavenger.

(14) The production method of (13), wherein the cation scavenger comprises a compound having a mercapto group and a carboxy group, or an indole compound having a carboxy group.

(15) The production method of (13), wherein the cation scavenger comprises a compound having one mercapto group and one or two carboxy groups.

(16) The production method of (13), wherein the cation scavenger is thiomalic acid or 3-mercaptopropionic acid.

(17) The production method of (1), wherein the protecting group removable under conditions different from those for the temporary protecting group of the morpholine ring nitrogen atom is a silyl protecting group.

(18) The production method of (1), wherein the protecting group removable under conditions different from those for the temporary protecting group of the morpholine ring nitrogen atom is a tert-butyldimethylsilyl group, a diisopropylphenylsilyl group, a triphenylsilyl group, or a diphenyl tert-butoxysilyl group.

(19) The production method of any of (1) to (18), wherein p is 1.

(20) The production method of any of (1) to (19), wherein the protecting group having an alkyl group having not less than 10 and not more than 300 carbon atoms and/or an alkenyl group having not less than 10 and not more than 300 carbon atoms is a group represented by the formula (II):

Z—Y-L-    (II)

wherein
L is a single bond, or a group represented by the formula (a1):

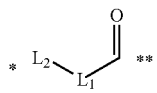

(a1)

wherein * indicates the bonding position to Y;
** indicates the bonding position to an oxygen atom or a nitrogen atom to be protected;
$L_1$ is an optionally substituted divalent $C_{1-22}$ hydrocarbon group; and
$L_2$ is C(=O) or a group represented by *N($R^3$)—$R^1$—N($R^2$)C(=O) (wherein  indicates the bonding position to $L^1$, * indicates the bonding position to Y, $R^1$ is an optionally substituted $C_{1-22}$ alkylene group, $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond);
Y is a single bond, an oxygen atom or NR (wherein R is a hydrogen atom, an alkyl group or an aralkyl group); and
Z is a group represented by the formula (a2):

(a2)

wherein * indicates the bonding position to Y;
ring A is a benzene ring or a cyclohexane ring;
$R^4$ is a hydrogen atom, or when $R_b$ is a group represented by the following formula (a3) and both ring A and ring B are benzene rings, $R^4$ is optionally a single bond or O— in combination with $R^6$ to form a fluorenyl group or a xanthenyl group together with ring B;
Q in the number of k are each independently a single bond, or —O—, —S—, —OC(=O)—, —NHC(=O)— or —NH—;
$R^5$ in the number of k are each independently an organic group having an alkyl group having not less than 10 and not more than 300 carbon atoms and/or an alkenyl group having not less than 10 and not more than 300 carbon atoms;
k is an integer of 1 to 4;
ring A optionally further has, in addition to $QR^5$ in the number of k, a substituent selected from the group consisting of a halogen atom, a $C_{1-6}$ alkyl group optionally substituted by a halogen atom(s), and a $C_{1-6}$ alkoxy group optionally substituted by a halogen atom(s);

$R_a$ is a hydrogen atom;
$R_b$ is a hydrogen atom, or a group represented by the formula (a3):

(a3)

wherein * indicates a bonding position;
ring B is a benzene ring or a cyclohexane ring;
j is an integer of 0 to 4;
Q in the number of j are as defined above;
$R^7$ in the number of j are each independently an organic group having an alkyl group having not less than 10 and not more than 300 carbon atoms and/or an alkenyl group having not less than 10 and not more than 300 carbon atoms;
$R^6$ is a hydrogen atom, or optionally a single bond or O— in combination with $R^4$ to form a fluorenyl group or a xanthenyl group together with ring A; and
ring B optionally further has, in addition to $QR^7$ in the number of j, a substituent selected from the group consisting of a halogen atom, a $C_{1-6}$ alkyl group optionally substituted by a halogen atom(s), and a $C_{1-6}$ alkoxy group optionally substituted by a halogen atom(s)), or
$R_a$ and $R_b$ are joined to form a carbonyl group.

(21) The production method of any of (1) to (20), further comprising the following step;
a step of removing all protecting groups from the n+p-mer morpholino oligonucleotide obtained by the step (step (2)) described in [1] (hereinafter to be referred to as "step (4)").

(22) The production method of any of (1) to (21), wherein the temporary protecting group removable under acidic conditions is a trityl group, a dimethoxytrityl group, or a monomethoxytrityl group.

(23) The production method of any of (1) to (22), wherein the non-polar solvent is selected from the group consisting of a halogenated solvent, an aromatic solvent, an ester solvent, an aliphatic solvent, a non-polar ether solvent, and a combination of these.

(24) The production method of any of (12) to (23), wherein the reaction mixture obtained by the step (step (1)) described in (12) is directly used in the step (step (2)) described in (1), without isolation of the morpholino oligonucleotide.

(25) A method of producing an n-mer morpholino oligonucleotide (n is any integer of one or more) wherein a morpholine ring nitrogen atom is not protected, comprising a step of reacting, in a non-polar solvent, an n-mer morpholino oligonucleotide wherein a morpholine ring nitrogen atom is protected by a temporary protecting group removable under acidic conditions,
and 5'-terminus is protected by a protecting group having an alkyl group having not less than 10 and not more than 300 carbon atoms and/or an alkenyl group having not less than 10 and not more than 300 carbon atoms or a protecting group removable under conditions different from those for the aforementioned protecting group of the morpholine ring nitrogen atom, with an acid in the presence of a cation scavenger to remove the temporary protecting group of the morpholine ring nitrogen atom (step (1)).

(26) The production method of (25), wherein the cation scavenger comprises a compound having a mercapto group and a carboxy group, or an indole compound having a carboxy group.

(27) The production method of (25), wherein the cation scavenger comprises a compound having one mercapto group and one or two carboxy groups.

(28) The production method of (25), wherein the cation scavenger is thiomalic acid or 3-mercaptopropionic acid.

(29) The production method of (1), wherein at least one of the nucleic acid bases of the p-mer morpholino oligonucleotide and the n-mer morpholino oligonucleotide is protected by a protecting group having an alkyl group having not less than 10 and not more than 300 carbon atoms and/or an alkenyl group having not less than 10 and not more than 300 carbon atoms.

(30) The production method of (29), wherein the protecting group having an alkyl group having not less than 10 and not more than 300 carbon atoms and/or an alkenyl group having not less than 10 and not more than 300 carbon atoms is a protecting group having a branched chain alkyl group having not less than 10 and not more than 300 carbon atoms and/or a branched chain alkenyl group having not less than 10 and not more than 300 carbon atoms.

(31) A morpholino nucleotide represented by the formula (I):

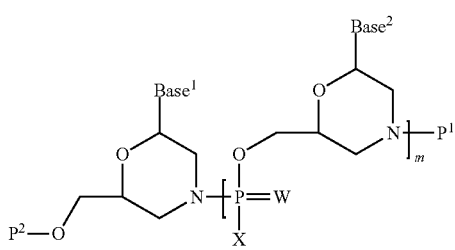

wherein
m is any integer of not less than 0,
$P^1$ is a hydrogen atom, or a temporary protecting group removable under acidic conditions,
$P^2$ is a protecting group having an alkyl group having not less than 10 and not more than 300 carbon atoms and/or an alkenyl group having not less than 10 and not more than 300 carbon atoms or a protecting group removable under conditions different from those for $P^1$,
$Base^1$ is a nucleic acid base optionally protected by a protecting group,
$Base^2$ in the number of m are each independently a nucleic acid base optionally protected by a protecting group,
X in the number of m are each independently a di $C_{1-6}$ alkylamino group, or a 1-piperazinyl group wherein a nitrogen atom at the 4-position is protected by a protecting group and further optionally substituted, and
W in the number of m are each an oxygen atom, provided that 1) at least one of the protecting group when $Base^1$ is protected by a protecting group, any protecting group when any $Base^2$ in the number of m are protected by a protecting group, and a protecting group for $P^2$ is a protecting group having an alkyl group having not less than 10 and not more than 300 carbon atoms and/or an alkenyl group having not less than 10 and not more than 300 carbon atoms, and 2) when $P^2$ is a protecting group having a linear alkyl group having not less than 10 and not more than 300 carbon atoms and/or a linear alkenyl group having not less than 10 and not more than 300 carbon atoms, at least one of $Base^1$ and any $Base^2$ in the number of m is a nucleic acid base protected by a protecting group having an alkyl group having not less than 10 and not more than 300 carbon atoms and/or an alkenyl group having not less than 10 and not more than 300 carbon atoms].

(32) The morpholino nucleotide of (31), wherein m is an integer of 0 to 19.

(33) The morpholino nucleotide of (31) or (32), wherein the protecting group having an alkyl group having not less than 10 and not more than 300 carbon atoms and/or an alkenyl group having not less than 10 and not more than 300 carbon atoms is a group represented by the formula (II):

L is a single bond, or a group represented by the formula (a1):

wherein * indicates the bonding position to Y;
** indicates the bonding position to an oxygen atom or a nitrogen atom to be protected;
$L^1$ is an optionally substituted divalent $C_{1-22}$ hydrocarbon group; and
$L^2$ is C(=O) or a group represented by N($R^3$)—$R^1$—N($R^2$)C(=O) (wherein  indicates the bonding position to $L^1$, * indicates the bonding position to Y, $R^1$ is an optionally substituted $C_{1-22}$ alkylene group, $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond);
Y is a single bond, an oxygen atom or NR (wherein R is a hydrogen atom, an alkyl group or an aralkyl group); and
Z is a group represented by the formula (a2):

wherein * indicates the bonding position to Y;
ring A is a benzene ring or a cyclohexane ring;
$R^4$ is a hydrogen atom, or when $R_b$ is a group represented by the following formula (a3) and both ring A and ring B are benzene rings, $R^4$ is optionally a single bond or O— in combination with $R^6$ to form a fluorenyl group or a xanthenyl group together with ring B;
Q in the number of k are each independently a single bond, or —O—, —S—, —OC(=O)—, —NHC(=O)— or —NH—;
$R^5$ in the number of k are each independently an organic group having an alkyl group having not less than 10 and not more than 300 carbon atoms and/or an alkenyl group having not less than 10 and not more than 300 carbon atoms;
k is an integer of 1 to 4;

ring A optionally further has, in addition to QR$^5$ in the number of k, a substituent selected from the group consisting of a halogen atom, a C$_{1-6}$ alkyl group optionally substituted by a halogen atom(s), and a C$_{1-6}$ alkoxy group optionally substituted by a halogen atom(s);

R$_a$ is a hydrogen atom;

R$_b$ is a hydrogen atom, or a group represented by the formula (a3):

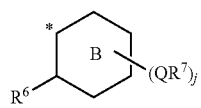

(a3)

wherein * indicates a bonding position;

ring B is a benzene ring or a cyclohexane ring;

j is an integer of 0 to 4;

Q in the number of j are as defined above;

R$^7$ in the number of j are each independently an organic group having an alkyl group having not less than 10 and not more than 300 carbon atoms and/or an alkenyl group having not less than 10 and not more than 300 carbon atoms;

R$^6$ is a hydrogen atom, or optionally a single bond or O— in combination with R$^4$ to form a fluorenyl group or a xanthenyl group together with ring A; and ring B optionally further has, in addition to QR$^7$ in the number of j, a substituent selected from the group consisting of a halogen atom, a C$_{1-6}$ alkyl group optionally substituted by a halogen atom(s), and a C$_{1-6}$ alkoxy group optionally substituted by a halogen atom(s)), or R$_a$ and R$_b$ are joined to form a carbonyl group.

(34) The morpholino nucleotide of (31) or (32), wherein the protecting group having an alkyl group having not less than 10 and not more than 300 carbon atoms and/or an alkenyl group having not less than 10 and not more than 300 carbon atoms is selected from the group consisting of a 3,4,5-tri(octadecyloxy)benzoyl group and a 3,4,5-tri(2',3'-dihydrophytyloxy)benzoyl group.

(35) The morpholino nucleotide of any of (31) to (34), wherein P$^2$ is a silyl protecting group.

(36) The morpholino nucleotide of any of (31) to (35), wherein P$^2$ is a tert-butyldimethylsilyl group, a diisopropylphenylsilyl group, a triphenylsilyl group, or a diphenyl tert-butoxysilyl group.

(37) The morpholino nucleotide of any of (31) to (36), wherein P$^1$ is a trityl group, a monomethoxytrityl group, or a dimethoxytrityl group.

Effect of the Invention

According to the present invention, in the liquid-phase synthesis of an morpholino oligonucleotide, the starting material, morpholino nucleoside monomer, remaining after condensation reaction and impurities derived from protecting group, which are caused by deprotection before condensation reaction, can be conveniently removed to the aqueous layer side by an extraction operation, and side reactions due to the impurities can also be suppressed, thus enabling efficient production of high quality morpholino oligonucleotide in large amounts.

Also, in particular, by protecting a hydroxyl group and an amino group particularly present at the 5'-terminus, and/or a nucleic acid base with a protecting group having a branched chain alkyl group having not less than 10 and not more than 300 carbon atoms and/or a branched chain alkenyl group having not less than 10 and not more than 300 carbon atoms, preferably by protecting a nucleic acid base with such a protecting group, or preferably with a protecting group having a branched chain alkyl group and/or a branched chain alkenyl group, a condensation reaction and deprotection reaction preferably proceed, and further, the solubility and phase separating ability of morpholino oligonucleotide in an extraction operation are improved, and work-up can be performed more efficiently.

That is, according to the present invention, by performing a condensation reaction in the liquid phase, the reactivity is strikingly improved as compared to the solid-phase method, monomer equivalents to be used can be strikingly reduced, and morpholino oligonucleotide can be conveniently isolated and purified by an extraction operation after the reaction. Therefore, morpholino oligonucleotide having a chain length utilizable as a pharmaceutical product can be produced efficiently and in a high yield by a liquid-phase synthesis process.

DETAILED DESCRIPTION OF THE PREFERRED EMBODIMENTS

Explanation of Terms

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the specification are hereby incorporated by reference so as to describe and disclose constructed products and methodology described in, for example, publications usable in relation to the described invention.

In the present specification, the "morpholino nucleoside" to be a constitutional unit of morpholino oligonucleotide is a compound represented by the following formula (1).

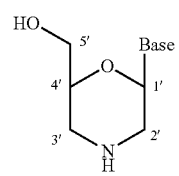

(1)

wherein Base is an optionally protected nucleic acid base.

Morpholino nucleoside (1) can be prepared by a method known per se (e.g., the method described in WO 91/09033A1, which is incorporated herein by reference in its entirety), or a method analogous thereto. Specifically, as shown in the following scheme, the corresponding ribonucleoside (2) is subjected to oxidative ring-opening with sodium periodate etc. to give the corresponding 2',3'-dialdehyde (3), the 2',3'-dialdehyde (3) is subjected to ring-closing with ammonia to give 2',3'-dihydroxymorpholino nucleoside (4), and the 2',3'-dihydroxymorpholino nucleoside (4) is reduced with a reducing agent (e.g., sodium cyanoborohydride, sodium triacetoxyborohydride and the like), whereby morpholino nucleoside (1) can be obtained.

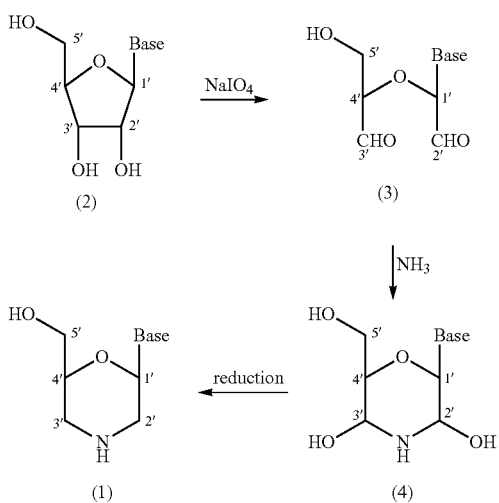

In the present specification, the position numbers (1', 2' and the like) of morpholino nucleoside correspond to the position numbers of carbon atoms of the ribose of the starting material, ribonucleoside (2).

In the present specification, morpholino oligonucleotide means a compound wherein two or more morpholino nucleosides are polymerized by phosphoramidate bonding or phosphorodiamidate bonding via a 5'-hydroxy group and the nitrogen atom of a morpholine ring. For example, as m'+1-mer morpholino oligonucleotide, a compound represented by the following formula (5) can be mentioned.

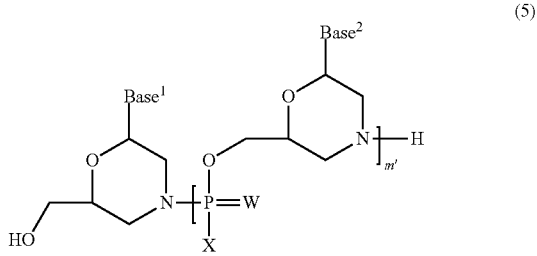

wherein m' is any integer of one or more,

Base$^1$ and Base$^2$ in the number of m' are each independently an optionally protected nucleic acid base, X in the number of m' are each independently a di-$C_{1-6}$ alkylamino group, or a 1-piperazinyl group wherein a nitrogen atom at the 4-position is protected by a protecting group and further optionally substituted, and the like, and W in the number of m' is an oxygen atom).

In the present specification, the "1-piperazinyl group wherein a 4-position nitrogen atom is protected by a protecting group and further optionally substituted" means that the 4-position nitrogen atom of the piperazinyl group is protected by a protecting group, and a 1-piperazinyl group protected by a protecting group sustainable under the deprotection conditions of the morpholine ring nitrogen atom of morpholino nucleotide is preferable. As the "protecting group of the 4-position nitrogen atom of the piperazinyl group", an acyl group is preferable and, for example, an acyl group having a fluoro group in the carbon chain such as monofluoroacetyl group, difluoroacetyl group, trifluoroacetyl group, 2-fluoropropionyl group, 2,2-difluoropropionyl group, 3,3,3-trifluoropropionyl group, 2,3,3,3-tetrafluoropropionyl group, pentafluoropropionyl group and the like is more preferable (see WO 2008/008113, which is incorporated herein by reference in its entirety). In the piperazinyl group, a hydrogen atom bonded to the carbon atom of the piperazinyl group may be substituted, and examples of the substituent include an alkyl group (preferably having 1 to 3 carbon atoms) such as methyl group and the like, and the like.

In the present specification, morpholino nucleoside at the terminus on the side having a free hydroxy group at the 5'-position of morpholino oligonucleotide (lower left side of the above-mentioned formula (5)) is referred to as the "5'-terminus", and morpholino nucleoside at the terminus on the opposite side (upper right side of the above-mentioned formula (5)) is referred to as the "3'-terminus", according to the usual practice in the nucleic acid chemistry.

In the present specification, the "nucleic acid base" is not particularly limited as long as it can be used for the synthesis of nucleic acid and includes, for example, a pyrimidine base such as cytosyl group, uracil group, thyminyl group, and the like, and a purine base such as adenyl group, guanyl group, and the like. Plural nucleic acid bases present in morpholino nucleotide may be heterogeneous nucleic acid bases or allogeneic nucleic acid bases. The "optionally protected nucleic acid base" means, for example, a nucleic acid base wherein an amino group and a hydroxyl group on the nucleic acid base are protected and, for example, that an amino group may be protected in an adenyl group, a guanyl group, or a cytosyl group, which is a nucleic acid base having an amino group, and a nucleic acid base wherein the amino group therein is protected by a protecting group sustainable under the deprotection conditions of the morpholine ring nitrogen atom of the morpholino nucleotide is preferable. The "amino-protecting group" is not particularly limited, and examples thereof include the protecting groups described in Greene's PROTECTIVE GROUPS IN ORGANIC SYNTHESIS, 4th edition, Wiley-Interscience, 2006, which is incorporated herein by reference in its entirety, and the like. Specific examples of the "amino-protecting group" include a pivaloyl group, a pivaloyloxymethyl group, a trifluoroacetyl group, a phenoxyacetyl group, a 4-isopropylphenoxyacetyl group, a 4-tert-butylphenoxyacetyl group, an acetyl group, a benzoyl group, an isobutyryl group, a dimethylformamidinyl group, a 9-fluorenylmethyloxycarbonyl group and the like. Among them, a phenoxyacetyl group, a 4-isopropylphenoxyacetyl group, an acetyl group, a benzoyl group, an isobutyryl group and a dimethylformamidinyl group are preferable. In addition, the carbonyl group of the nucleic acid base is optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, 2-(phenylsulfonyl)ethanol, 2-cyanoethanol, 2-(trimethylsilyl) ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride, and the like. In some cases, the carbonyl-protecting group does not need to be particularly introduced. Moreover, in addition to the above-mentioned groups, a modified nucleic acid base (e.g., a 8-bromoadenyl group, a 8-bromoguanyl group, a 5-bromocytosyl group, a 5-iodocytosyl group, a 5-bromouracil group, a 5-iodouracil group, a 5-fluorouracil group, a 5-methylcytosyl group, a 8-oxoguanyl group, a hypoxanthinyl group etc.), which is a nucleic acid base substituted by any 1 to 3 substituents (e.g., a halogen atom, an alkyl group, an aralkyl group, an alkoxy group, an acyl group, an alkoxyalkyl group, a hydroxy group, an amino group, a monoalkylamino group, a dialkylamino group, a carboxy group, a cyano group, a nitro group etc.) at any position(s), are also encompassed in the "nucleic acid base".

Also, the "amino-protecting group" includes a protecting group having an alkyl group having not less than 10 and not more than 300 carbon atoms and/or an alkenyl group having not less than 10 and not more than 300 carbon atoms, and the amino group can be protected according to a method known per se or a method analogous thereto. For example, it can be protected by reacting a nitrogen atom on the pyrimidine ring of a thyminyl group with 3,4,5-tri(octadecyloxy)benzoyl chloride in the presence of a base.

In the present specification, the "halogen atom" means a fluorine atom, a chlorine atom, a bromine atom or iodine atom.

In the present specification, examples of the "alkyl (group)" include a linear or branched chain alkyl group having one or more carbon atoms. When the carbon number is not particularly limited, it is preferably a $C_{1-10}$ alkyl group, more preferably a $C_{1-6}$ alkyl group. When the carbon number is not particularly limited, for example, methyl, ethyl, propyl, isopropyl, butyl, isobutyl, sec-butyl, tert-butyl, pentyl, hexyl and the like are preferable, and methyl and ethyl are particularly preferable.

In the present specification, the "aralkyl (group)" means a $C_{7-20}$ aralkyl group, preferably a $C_{7-16}$ aralkyl group ($C_{6-10}$ aryl-$C_{1-6}$ alkyl group). Specific preferable examples include benzyl, 1-phenylethyl, 2-phenylethyl, 1-phenylpropyl, naphthylmethyl, 1-naphthylethyl, 1-naphthylpropyl and the like, and benzyl is particularly preferable.

In the present specification, examples of the "alkoxy (group)" include an alkoxy group having one or more carbon atoms. When the carbon number is not particularly limited, it is preferably a $C_{1-10}$ alkoxy group, more preferably a $C_{1-6}$ alkoxy group. When the carbon number is not particularly limited, methoxy, ethoxy, propoxy, isopropoxy, butoxy, isobutoxy, sec-butoxy, tert-butoxy, pentyloxy, hexyloxy and the like are preferable, and methoxy and ethoxy are particularly preferable.

In the present specification, examples of the "acyl (group)" include a linear or branched chain $C_{1-6}$ alkanoyl group, a $C_{7-13}$ aroyl group and the like. Specific examples thereof include formyl, acetyl, n-propionyl, isopropionyl, n-butyryl, isobutyryl, pivaloyl, valeryl, hexanoyl, benzoyl, naphthoyl, levulinyl and the like, each of which is optionally substituted.

In the present specification, examples of the "alkenyl (group)" include a linear or branched chain $C_{2-6}$ alkenyl group and the like. Examples thereof include vinyl, 1-propenyl, allyl, isopropenyl, butenyl, isobutenyl and the like. Among them, a $C_{2-4}$ alkenyl group is preferable.

In the present specification, preferable examples of the "alkynyl (group)" include a $C_{2-6}$ alkynyl group and the like. Examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Among them, a $C_{2-4}$ alkynyl group is preferable.

In the present specification, the "cycloalkyl (group)" means a cyclic alkyl group, and examples thereof include cyclopropyl, cyclobutyl, cyclopentyl, cyclohexyl, cycloheptyl, cyclooctyl and the like. Among them, a $C_{3-6}$ cycloalkyl group such as cyclopropyl, cyclobutyl, cyclopentyl, cyclohexyl and the like is preferable, and cyclohexyl is particularly preferable.

In the present specification, the "aryl (group)" means a monocyclic aromatic or polycyclic (fused) aromatic hydrocarbon group. Specific examples thereof include a $C_{6-14}$ aryl group such as phenyl, 1-naphthyl, 2-naphthyl, biphenylyl, 2-anthryl and the like, and the like. Among them, a $C_{6-10}$ aryl group is more preferably and phenyl is particularly preferable.

In the present specification, examples of the "hydrocarbon group" include an aliphatic hydrocarbon group, an aromatic-aliphatic hydrocarbon group, a monocyclic saturated hydrocarbon group, an aromatic hydrocarbon group and the like, and specific examples thereof include monovalent groups such as an alkyl group, an alkenyl group, an alkynyl group, a cycloalkyl group, an aryl group, an aralkyl group and the like and a divalent group derived therefrom.

In the present specification, the "organic group having a hydrocarbon group" means a group having the aforementioned "hydrocarbon group", and the moiety other than the "hydrocarbon group" of the "organic group having a hydrocarbon group" can be determined freely. For example, the organic group optionally has, as a linker, a moiety such as —O—, —S—, —COO—, —OCONH—, —CONH— and the like.

In the present specification, the "substituent" of the "optionally substituted" encompasses the aforementioned halogen atom, alkyl group, aralkyl group, alkoxy group, acyl group, alkenyl group, alkynyl group, cycloalkyl group, aryl group, as well as hydroxy group, nitro group, a cyano group, guanidyl group, a carboxy group, alkoxycarbonyl group (the alkoxy moiety is the same as that in the aforementioned alkoxy group), sulfo group, phospho group, alkylthio group (the alkyl moiety is the same as that in the aforementioned alkyl group), alkylsulfinyl group (the alkyl moiety is the same as that in the aforementioned alkyl group), alkylsulfonyl group (the alkyl moiety is the same as that in the aforementioned alkyl group), amino group, monoalkylamino group (the alkyl moiety is the same as that in the aforementioned alkyl group), dialkylamino group (the alkyl moiety is the same as that in the aforementioned alkyl group), oxo group and the like.

Morpholino nucleotide wherein 5'-terminus and/or nucleic acid base are/is optionally protected by particular protecting group, and morpholine ring nitrogen atom is optionally protected by temporary protecting group removable under acidic conditions.

Using morpholino nucleotide wherein 5'-terminus (e.g., 5'-position hydroxyl group or hydroxyl group and/or amino group present on the substituent of 5'-position hydroxyl group) and/or a nucleic acid base are/is optionally protected by a particular protecting group used in the present invention, a production method of a morpholino oligonucleotide suitable for liquid-phase synthesis can be provided.

Since high efficiency and high yield can be achieved in the production method of the objective morpholino oligonucleotide, a morpholino nucleotide wherein the 5'-position hydroxyl group or a hydroxyl group present on the substituent of 5'-position hydroxyl group and/or a nucleic acid base is or are optionally protected by a protecting group having an alkyl group having not less than 10 and not more than 300 carbon atoms and/or an alkenyl group having not less than 10 and not more than 300 carbon atoms (anchor) is preferable.

Of these, since higher efficiency and higher yield can be achieved in the production method of the objective morpholino oligonucleotide, a morpholino nucleotide wherein a nucleic acid base is protected by a protecting group having an alkyl group having not less than 10 and not more than 300 carbon atoms and/or an alkenyl group having not less than 10 and not more than 300 carbon atoms is preferable. As the protecting group having an alkyl group having not less than 10 and not more than 300 carbon atoms and/or an alkenyl group having not less than 10 and not more than 300 carbon atoms, a protecting group having a branched chain alkyl group having not less than 10 and not more than 300 carbon atoms and/or a branched chain alkenyl group having not less than 10 and not more than 300 carbon atoms is preferable and, particularly, a morpholino nucleotide wherein a nucleic acid base is protected by a protecting group having a branched chain alkyl group having not less than 10 and not more than 300 carbon atoms and/or a branched chain alkenyl group having not less than 10 and not more than 300 carbon atoms is preferable.

The "5'-hydroxy group has a substituent having a hydroxy group" means that the hydrogen atom of the 5'-hydroxy group is substituted by a substituent having a hydroxy group. The "substituent" of the "substituent having a hydroxy group" is not particularly limited as long as the main chain is constituted of 1 to 20 atoms. Here, the "main chain" means a shortest atom chain linking the oxygen atom of the 5'-hydroxy group and the oxygen atom of the hydroxy group on the substituent, and the atom chain is optionally further substituted. The atom constituting the main chain is selected from carbon atom, oxygen atom, nitrogen atom, sulfur atom, phosphorus atom and the like. Specific examples of the "substituent having a hydroxy group" include organic groups having a hydrocarbon group such as alkyl group, aralkyl group, acyl group, alkenyl group, alkynyl group, cycloalkyl group, aryl group, alkoxycarbonyl group and the like, wherein the hydrogen atom on the hydrocarbon group is substituted by a hydroxy group and the like. In addition, for example, the substituent of the following 5'-hydroxy group disclosed in WO 2008/008113, which is incorporated herein by reference in its entirety, and the like can be mentioned. When the 5'-position hydroxyl group has a substituent having an amino group, it means that a hydrogen atom of a 5'-position hydroxyl group is substituted by a substituent having an amino group, and others are as defined above.

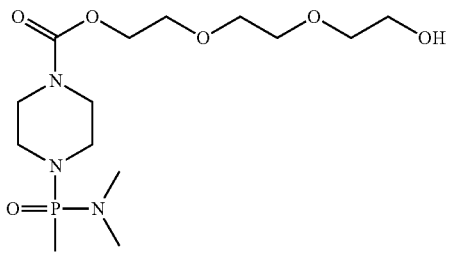 [SMILES: CN(C)P(C)(=O)N1CCN(C(=O)OCCOCCOCCO)CC1]

Examples of the "alkyl group having not less than 10 and not more than 300 carbon atoms and/or alkenyl group having not less than 10 and not more than 300 carbon atoms" include a monovalent groups and divalent groups derived therefrom. Among them, alkyl group having 10 to 40 carbon atoms is preferable, and alkyl group having 10 to 30 carbon atoms is particularly preferable. The alkyl group and the alkenyl group of the "alkyl group having not less than 10 and not more than 300 carbon atoms and/or alkenyl group having not less than 10 and not more than 300 carbon atoms" include linear or branched chain alkyl group, and linear or branched chain alkenyl group. In the production method of the present invention, branched chain alkyl group and branched chain alkenyl group are preferable, and branched chain alkyl group is particularly preferable. Specific preferable examples of the "alkyl group having not less than 10 and not more than 300 carbon atoms and/or alkenyl group having not less than 10 and not more than 300 carbon atoms" include branched chain alkyl groups or branched chain alkenyl groups such as 3,7,11,15-tetramethylhexadecyl group, 3,7,11-trimethyldodecyl group, 2,6,10,14-tetramethylpentadecyl group, 2,6,10-trimethylundecyl group, 2,2,4,8,10,10-hexamethyl-5-undecyl group, 2,6,10-trimethylundeca-1,5,9-trienyl group, 2,6-dimethylheptyl group, 2,6-dimethylhepta-5-enyl group, 2,6-dimethylhepta-1,5-dienyl group, 9-nonadecyl group, 12-methyltridecyl group, 11-methyltridecyl group, 11-methyldodecyl group, 10-methylundecyl group, 8-heptadecyl group, 7-pentadecyl group, 7-methyloctyl group, 3-methyloctyl group, 3,7-dimethyloctyl group, 3-methylheptyl group, 3-ethylheptyl group, 5-undecyl group, 2-heptyl group, 2-methyl-2-hexyl group, 2-hexyl group, 3-heptyl group, 4-heptyl group, 4-methylpentyl group, 3-methylpentyl group, 2,4,4-trimethylpentyl group, and the like, linear alkyl groups of monovalent aliphatic hydrocarbon group such as octadecyl group, heptadecyl group, hexadecyl group, pentadecyl group, tetradecyl group, tridecyl group, dodecyl group, undecyl group, decyl group, nonyl group, octyl group, heptyl group, hexyl group, pentyl group and the like, and divalent groups derived therefrom.

As the morpholino oligonucleotide wherein a 5'-hydroxy group or a hydroxy group present on a substituent of the 5'-hydroxy group and/or a nucleic acid base may be protected by a protecting group having an alkyl group having not less than 10 and not more than 300 carbon atoms and/or an alkenyl group having not less than 10 and not more than 300 carbon atoms, and the morpholine ring nitrogen atom is optionally protected by a temporary protecting group removable under acidic conditions, specifically, a compound represented by the following formula (I) (hereinafter sometimes to be referred to as the compound of the present invention) can be mentioned.

The formula (I):

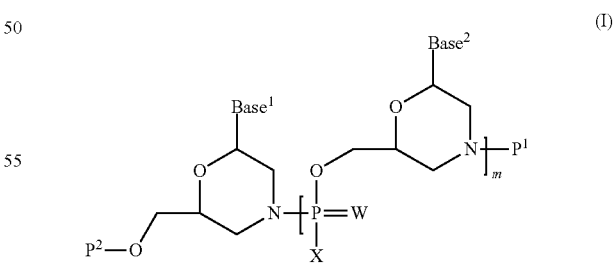

wherein m is any integer of not less than 0, $P^1$ is a hydrogen atom, or a temporary protecting group removable under acidic conditions, $P^2$ is a protecting group having an alkyl group having not less than 10 and not more than 300 carbon atoms and/or an alkenyl group having not less than 10 and not more than 300 carbon atoms or a protecting group removable under conditions different from those for $P^1$, Base$^1$ is a nucleic acid base optionally protected by a protecting group, Base$^2$ in the number of m are each independently a nucleic acid base optionally protected by a protecting group, X in the number of m are each independently a di-$C_{1-6}$ alkylamino group, or a 1-piperazinyl group wherein a nitrogen atom at the 4-position is protected by a protecting group and further optionally substituted, and W in the number of m are each an oxygen atom.

In the below-mentioned production method of the morpholino oligonucleotide of the present invention, the 5'-hydroxy group is activated phosphoramidated, and the morpholine ring nitrogen atom is bonded to p-mer morpholino oligonucleotide (p is any integer of one or more) protected by a temporary protecting group removable under acidic conditions, whereby the compound of the present invention can form m+1+p-mer morpholino oligonucleotide (p is any integer of one or more).

When m is 0, the compound of the present invention is understood to be a "morpholino nucleoside", which is a starting compound of the 5'-terminus in the synthesis of the morpholino oligonucleotide of the present invention. In addition, the compound of the present invention also encompasses one wherein the morpholine ring nitrogen atom on the 3'-terminus side is unprotected ($P^1$ is a hydrogen atom) in a broad sense.

In the above-mentioned formula (I), m is any integer of not less than 0, preferably, 0. While the upper limit of m is not particularly limited, it is preferably 49 or less, more preferably 29 or less, further preferably 19 or less.

The temporary protecting group $P^1$ that can be used as the protecting group of the morpholine ring nitrogen atom at the 3'-terminus of the present invention is not particularly limited as long as it can be deprotected under acidic conditions and can be used as a hydroxy-protecting group. Examples thereof include a trityl group, 9-(9-phenyl)xanthenyl group, a 9-phenylthioxanthenyl group, di($C_{1-6}$ alkoxy)trityl groups such as a 1,1-bis(4-methoxyphenyl)-1-phenylmethyl group, a dimethoxytrityl group and the like, mono($C_{1-18}$ alkoxy) trityl groups such as 1-(4-methoxyphenyl)-1,1-diphenylmethyl group, monomethoxytrityl group and the like, and the like can be mentioned. Among these, a trityl group, a monomethoxytrityl group and a dimethoxytrityl group are preferable, and a trityl group and dimethoxytrityl group are more preferable, in view of easiness of deprotection and easy availability.

The protecting group $P^2$ that can be used as the 5'-position hydroxyl-protecting group of the compound of the present invention is not particularly limited as long as it is deprotectable under conditions different from those for $P^1$ and can be used as a hydroxyl-protecting group. For example, levulinyl group that can be removed by hydrazine, photo-removable protecting groups which can be removed by light such as o-nitrobenzyl group, benzophenone derivative, bromocoumarin derivative and the like, allyloxycarbonyl group (Alloc group) and benzyl group which are deprotectable by catalytic reduction using a palladium catalyst and the like, and silyl protecting group that can be removed by fluoride ion can be mentioned. Of these, a silyl protecting group is preferable. Examples of the silyl protecting group include tert-butyldimethylsilyl group, diisopropylphenylsilyl group, triphenylsilyl group, diphenyl tert-butoxysilyl group and the like. The protecting group $P^2$ may also be "a protecting group having an alkyl group having not less than 10 and not more than 300 carbon atoms and/or an alkenyl group having not less than 10 and not more than 300 carbon atoms" described above.

Base$^1$ and Base$^2$ in the number of m in the above-mentioned formula (I) are each independently an optionally protected nucleic acid base. The "optionally protected nucleic acid base" means, for example, that an amino group may be protected in an adenyl group, a guanyl group or a cytosyl group, which is a nucleic acid base having an amino group, or imide group is optionally protected in a thymyl group or an uracil group having a cyclic imide group, and a nucleic acid base wherein the amino group therein is protected by a protecting group sustainable under the deprotection conditions of the morpholine ring nitrogen atom is preferable. The protecting group of the "amino-protecting group" and the "imido-protecting group" is not particularly limited and, for example, any protecting groups described in Greene's PROTECTIVE GROUPS IN ORGANIC SYNTHESIS, 4th ed., JOHN WILLY&SONS (2006), which is incorporated herein by reference in its entirety, and the like can be mentioned. Specific examples of such "amino-protecting group" and "imide-protecting group" include a pivaloyl group, a pivaloyloxymethyl group, a trifluoroacetyl group, a phenoxyacetyl group, a 4-isopropylphenoxyacetyl group, a 4-tert-butylphenoxyacetyl group, an acetyl group, a benzoyl group, an isobutyryl group, a dimethylformamidinyl group, a 9-fluorenylmethyloxycarbonyl group and the like. Among them, a phenoxyacetyl group, a 4-isopropylphenoxyacetyl group, an acetyl group, a benzoyl group, an isobutyryl group and a dimethylformamidinyl group are preferable. In addition, the carbonyl group of the nucleic acid base is optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, 2-(phenylsulfonyl)ethanol, 2-cyanoethanol, 2-(trimethylsilyl) ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride, and the like. In some cases, the carbonyl-protecting group does not particularly need to be introduced.

The "optionally protected nucleic acid base" includes "a protecting group having an alkyl group having not less than 10 and not more than 300 carbon atoms and/or an alkenyl group having not less than 10 and not more than 300 carbon atoms" described above.

In the above-mentioned formula (I), a compound wherein 1) at least one of the protecting group when Base$^1$ is protected by a protecting group, any protecting group when any Base$^2$ in the number of m are protected by a protecting group, and a protecting group for $P^2$ is a protecting group having an alkyl group having not less than 10 and not more than 300 carbon atoms and/or an alkenyl group having not less than 10 and not more than 300 carbon atoms, and 2) when $P^2$ is a protecting group having a linear alkyl group having not less than 10 and not more than 300 carbon atoms and/or a linear alkenyl group having not less than 10 and not more than 300 carbon atoms, at least one of Base$^1$ and any Base$^2$ in the number of m is a nucleic acid base protected by a protecting group having an alkyl group having not less than 10 and not more than 300 carbon atoms and/or an alkenyl group having not less than 10 and not more than 300 carbon atoms is preferable.

In the above-mentioned formula (I), at least one of the protecting group when Base¹ is protected by a protecting group, and any protecting group when any Base² in the number of m are protected by a protecting group is preferably a protecting group having an alkyl group having not less than 10 and not more than 300 carbon atoms and/or an alkenyl group having not less than 10 and not more than 300 carbon atoms. As the protecting group P² in this case, the aforementioned silyl protecting group is preferable.

In the above-mentioned formula (I), the protecting group having an alkyl group having not less than 10 and not more than 300 carbon atoms and/or an alkenyl group having not less than 10 and not more than 300 carbon atoms is more preferably a protecting group having a branched chain alkyl group having not less than 10 and not more than 300 carbon atoms and/or a branched chain alkenyl group having not less than 10 and not more than 300 carbon atoms.

In the above-mentioned formula (I), X in the number of m are each independently a di-$C_{1-6}$ alkylamino group, or a 1-piperazinyl group wherein a nitrogen atom at the 4-position is protected by a protecting group and further optionally substituted, preferably a di-$C_{1-6}$ alkylamino group.

As the di-$C_{1-6}$ alkylamino group, a dimethylamino group, a diethylamino group, an N-ethyl-N-methylamino group and the like are preferable, and a dimethylamino group is preferable.

As the protecting group of the 4-position nitrogen atom of the piperazinyl group, an acyl group is preferable and, for example, an acyl group having a fluoro group in the carbon chain, such as a monofluoroacetyl group, a difluoroacetyl group, a trifluoroacetyl group, a 2-fluoropropionyl group, a 2,2-difluoropropionyl group, a 3,3,3-trifluoropropionyl group, a 2,3,3,3-tetrafluoropropionyl group, a pentafluoropropionyl group and the like, is more preferable. While the protecting group is generally deprotected after completion of the elongation reaction, the amino group of the piperazino group may be further modified, after deprotection, by a modifying group according to the method described in WO 2008/008113, which is incorporated herein by reference in its entirety. Examples of the modifying group include a halogen atom, an alkyl group, an aralkyl group, an alkoxy group, an acyl group, an alkenyl group, an alkynyl group, a cycloalkyl group, an aryl group, a hydroxy group, a nitro group, a cyano group, a guanidyl group, a carboxy group, an alkoxycarbonyl group, a sulfo group, a phospho group, an alkylthio group, an alkylsulfinyl group, an alkylsulfonyl group and the like. As the modifying group of the piperazinyl group, an optionally substituted acyl group is preferable, and an acyl group optionally substituted by a guanidyl group (e.g., 6-guanidinohexanoyl group) is more preferable. In the piperazinyl group, the hydrogen atom bonded to the carbon atom of the piperazinyl group may be substituted, and examples of the substituent include an alkyl group (preferably having 1 to 3 carbon atoms) such as a methyl group and the like, and the like.

W in the number of m are oxygen atoms.

When the protecting group for P² and/or the protecting group of Base¹ in the above-mentioned formula (I) are/is "a protecting group having an alkyl group having not less than 10 and not more than 300 carbon atoms and/or an alkenyl group having not less than 10 and not more than 300 carbon atoms", preferred as the protecting group is a protecting group represented by the following formula (II):

$$Z-Y-L- \qquad (II)$$

wherein
L is a single bond, or a group represented by the formula (a1):

wherein * indicates the bonding position to Y;
** indicates the bonding position to an oxygen atom or a nitrogen atom to be protected;
$L_1$ is an optionally substituted divalent $C_{1-22}$ hydrocarbon group; and
$L_2$ is C(=O) or a group represented by *N($R^3$)—$R^1$—N($R^2$)C(=O) (wherein  indicates the bonding position to $L^1$, * indicates the bonding position to Y, $R^1$ is an optionally substituted $C_{1-22}$ alkylene group, $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond), Y is a single bond, an oxygen atom or NR (wherein R is a hydrogen atom, an alkyl group or an aralkyl group), and
Z is a group represented by the formula (a2):

wherein * indicates the bonding position to Y;
ring A is a benzene ring or a cyclohexane ring;
$R^4$ is a hydrogen atom, or when $R_b$ is a group represented by the following formula (a3) and both ring A and ring B are benzene rings, $R^4$ is optionally a single bond or O— in combination with $R^6$ to form a fluorenyl group or a xanthenyl group together with ring B;
Q in the number of k are each independently a single bond, or —O—, —S—, —OC(=O)—, —NHC(=O)— or —NH—;
$R^5$ in the number of k are each independently an organic group having an alkyl group having not less than 10 and not more than 300 carbon atoms and/or an alkenyl group having not less than 10 and not more than 300 carbon atoms;
k is an integer of 1 to 4;
ring A optionally further has, in addition to QR⁵ in the number of k, a substituent selected from the group consisting of a halogen atom, a $C_{1-6}$ alkyl group optionally substituted by a halogen atom(s), and a $C_{1-6}$ alkoxy group optionally substituted by a halogen atom(s);
$R_a$ is a hydrogen atom;
$R_b$ is a hydrogen atom, or a group represented by the formula (a3):

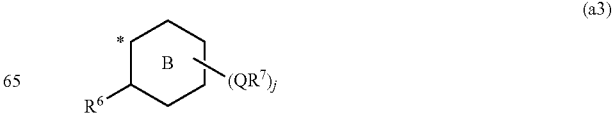

wherein * indicates a bonding position;

ring B is a benzene ring or a cyclohexane ring;

j is an integer of 0 to 4;

Q in the number of j are as defined above;

$R^7$ in the number of j are each independently an organic group having an alkyl group having not less than 10 and not more than 300 carbon atoms and/or an alkenyl group having not less than 10 and not more than 300 carbon atoms;

$R^6$ is a hydrogen atom, or optionally a single bond or O— in combination with $R^4$ to form a fluorenyl group or a xanthenyl group together with ring A; and ring B optionally further has, in addition to $QR^7$ in the number of j, a substituent selected from the group consisting of a halogen atom, a $C_{1-6}$ alkyl group optionally substituted by a halogen atom(s), and a $C_{1-6}$ alkoxy group optionally substituted by a halogen atom(s)), or $R_a$ and $R_b$ are joined to form a carbonyl group.

A preferable embodiment of the linker L represented by the above-mentioned formula (a1) is a group wherein, in the formula (a1), $L_1$ is an ethylene group or CH$_2$—O-1,4-phenylene-O—CH$_2$; and $L_2$ is C(=O), or a group represented by *N(R$^3$)—R$^1$—N(R$^2$)C(=O) (wherein  indicates the bonding position to $L_1$, * indicates the bonding position to Y, $R^1$ is a $C_{1-6}$ alkylene group, and $R^2$ and $R^3$ are each independently a hydrogen atom or an optionally substituted $C_{1-6}$ alkyl group, or $R^2$ and $R^3$ are optionally joined to form an optionally substituted $C_{1-6}$ alkylene bond.

Another preferable embodiment of the linker L represented by the above-mentioned formula (a1) is a group wherein, in the formula (a1), $L_1$ is an ethylene group; and $L_2$ is C(=O).

Another preferable embodiment of the linker L represented by the above-mentioned formula (a1) is a group wherein, in the formula (a1), $L_1$ is an ethylene group; and the moiety of N(R$^3$)—R$^1$—N(R$^2$) for $L_2$ is a piperazinylene group.

Another preferable embodiment of the linker L represented by the above-mentioned formula (a1) is a group wherein, in the formula (a1), $L_1$ is an ethylene group; and $L_2$ is a group represented by *N(R$^3$)—R$^1$—N(R$^2$)C(=O) wherein  indicates the bonding position to $L^1$, * indicates the bonding position to Y, $R^1$ is a pentylene group or a hexylene group, and $R^2$ and $R^3$ are each independently a hydrogen atom or a methyl group.

A particularly preferable example of the above-mentioned linker L is a single bond or a succinyl group since it is easily available and economical.

Y in the above-mentioned formula (I) is a single bond, an oxygen atom, or NR (wherein R is a hydrogen atom, an alkyl group or an aralkyl group).

In the present specification, the "alkyl group" for R is a $C_{1-30}$ alkyl group, preferably a $C_{1-10}$ alkyl group, more preferably a $C_{1-6}$ alkyl group. Specific preferable examples thereof include methyl, ethyl, propyl, isopropyl, butyl, isobutyl, sec-butyl, tert-butyl and the like, and methyl and ethyl are particularly preferable.

In the present specification, the "aralkyl group" for R is a $C_{7-30}$ aralkyl group, preferably a $C_{7-20}$ aralkyl group, more preferably a $C_{7-16}$ aralkyl group ($C_{6-10}$ aryl-$C_{1-6}$ alkyl group). Specific preferable examples thereof include benzyl, 1-phenylethyl, 2-phenylethyl, 1-phenylpropyl, α-naphthylmethyl, 1-(α-naphthyl)ethyl, 2-(α-naphthyl)ethyl, 1-(α-naphthyl)propyl, β-naphthylmethyl, 1-(β-naphthyl)ethyl, 2-(β-naphthyl)ethyl, 1-(β-naphthyl)propyl and the like, and benzyl is particularly preferable.

R is preferably a hydrogen atom, a $C_{1-6}$ alkyl group or a $C_{7-16}$ aralkyl group, more preferably a hydrogen atom, methyl, ethyl or benzyl, particularly preferably a hydrogen atom.

Y is preferably a single bond, an oxygen atom or NH.

A preferable embodiment of Z is a group represented by the formula (a2).

The preferable embodiment for Z in the above-mentioned formula (I), that is, a group represented by the formula (a2) for Z in the above-mentioned formula (I) is a particular benzyl group (in the formula (a2), ring A is a benzene ring, both $R_a$ and $R_b$ are hydrogen atoms, and $R^4$ is a hydrogen atom); a particular benzoyl group (in the formula (a2) wherein ring A is a benzene ring, $R_a$ and $R_b$ are joined to form an oxygen atom, and $R^4$ is a hydrogen atom); a particular diphenylmethyl group (in the formula (a2), ring A is a benzene ring, $R_a$ is a hydrogen atom, $R^4$ is a hydrogen atom, k is 1 to 3, and $R_b$ is a group represented by the formula (a3) (wherein ring B is a benzene ring, $R^6$ is a hydrogen atom, and j is 0 or 1)); a particular fluorenyl group (in the formula (a2), ring A is a benzene ring, $R_a$ is a hydrogen atom, k is 1, $R_b$ is a group represented by the formula (a3) (wherein ring B is a benzene ring, and j is 0)), and $R^6$ is a single bond in combination with $R^4$ to form a fluorene ring together with ring A); a particular xanthenyl group (in the formula (a2), ring A is a benzene ring, $R_a$ is a hydrogen atom, k is 1, $R_b$ is a group represented by the formula (a3) (wherein ring B is a benzene ring, and j is 0), and $R^6$ is —O— in combination with $R^4$ to form a xanthine ring together with ring A).

The ring A in the above-mentioned formula (a2) is a benzene ring or a cyclohexane ring, preferably a benzene ring.

In the $QR^5$ group in the number of k in the above-mentioned formula (a2), and the $QR^7$ group in the number of j in the formula (a3), Q is a single bond, or —O—, —S—, —OC(=O)—, —NHC(=O)— or —NH—, preferably —O—. The $QR^5$ group in the number of k, and $QR^7$ group in the number of j may be the same or different.

In the above-mentioned formula (a2), the "$R_a$ and $R_b$ are joined to form an oxygen atom" means that $R_a$ and $R_b$ are joined to form a carbonyl group (C(=O)).

The "organic group having an alkyl group having not less than 10 and not more than 300 carbon atoms and/or an alkenyl group having not less than 10 and not more than 300 carbon atoms" for $R^5$ or $R^7$ is a monovalent organic group having an alkyl group having not less than 10 and not more than 300 carbon atoms and/or an alkenyl group having not less than 10 and not more than 300 carbon atoms in the molecule structure thereof.

The carbon number of the "alkyl group having not less than 10 and not more than 300 carbon atoms and/or alkenyl group having not less than 10 and not more than 300 carbon atoms" of the "organic group having an alkyl group having not less than 10 and not more than 300 carbon atoms and/or an alkenyl group having not less than 10 and not more than 300 carbon atoms" is preferably 14 to 40, more preferably 14 to 30.

The moiety of the "alkyl group having not less than 10 and not more than 300 carbon atoms and/or alkenyl group having not less than 10 and not more than 300 carbon atoms" of the "organic group having an alkyl group having not less than 10 and not more than 300 carbon atoms and/or an alkenyl group having not less than 10 and not more than 300 carbon atoms" is not particularly limited, and it may be present at the terminus (monovalent group), or the other site (e.g., divalent group).

As the "alkyl group having not less than 10 and not more than 300 carbon atoms and/or alkenyl group having not less than 10 and not more than 300 carbon atoms", a monovalent group and a divalent group derived therefrom can be mentioned. Among them, an alkyl group having 14 to 40 carbon atoms is preferable, and an alkyl group having 14 to 30 carbon atoms is particularly preferable.

The alkyl group and the alkenyl group of the "alkyl group having not less than 10 and not more than 300 carbon atoms and/or an alkenyl group having not less than 10 and not more than 300 carbon atoms" include a linear or branched chain alkyl group and a linear or branched chain alkenyl group. In the production method of the present invention, a branched chain alkyl group or a branched chain alkenyl group is preferable, and a branched chain alkyl group is particularly preferable. Specific preferable examples of the "alkyl group having not less than 10 and not more than 300 carbon atoms and/or an alkenyl group having not less than 10 and not more than 300 carbon atoms" include a monovalent aliphatic hydrocarbon group of a branched chain alkyl group or branched chain alkenyl group such as 3,7,11,15-tetramethylhexadecyl group, 3,7,11-trimethyldodecyl group, 2,6,10,14-tetramethylpentadecyl group, 2,6,10-trimethylundecyl group, 2,2,4,8,10,10-hexamethyl-5-undecyl group, 2,6,10-trimethylundeca-1,5,9-trienyl group, 2,6-dimethylheptyl group, 2,6-dimethylhepta-5-enyl group, 2,6-dimethylhepta-1,5-dienyl group, 9-nonadecyl group, 12-methyltridecyl group, 11-methyltridecyl group, 11-methyldodecyl group, 10-methylundecyl group, 8-heptadecyl group, 7-pentadecyl group, 7-methyloctyl group, 3-methyloctyl group, 3,7-dimethyloctyl group, 3-methylheptyl group, 3-ethylheptyl group, 5-undecyl group, 2-heptyl group, 2-methyl-2-hexyl group, 2-hexyl group, 3-heptyl group, 4-heptyl group, 4-methylpentyl group, 3-methylpentyl group, 2,4,4-trimethylpentyl group and the like, or a linear alkyl group such as octadecyl group, heptadecyl group, hexadecyl group, pentadecyl group, tetradecyl group, tridecyl group, dodecyl group, undecyl group, decyl group, nonyl group, octyl group, heptyl group, a hexyl group, pentyl group and the like, and divalent groups derived therefrom.

In the "organic group having an alkyl group having not less than 10 and not more than 300 carbon atoms and/or an alkenyl group having not less than 10 and not more than 300 carbon atoms", the moiety other than the "alkyl group having not less than 10 and not more than 300 carbon atoms and/or alkenyl group having not less than 10 and not more than 300 carbon atoms" can be determined freely. For example, it optionally has a moiety such as —O—, —S—, —COO—, —OCONH—, and —CONH—, and a hydrocarbon group (monovalent group or divalent group) and the like as a linker. Examples of the "hydrocarbon group" include an aliphatic hydrocarbon group, an aromatic aliphatic hydrocarbon group, a monocyclic saturated hydrocarbon group, an aromatic hydrocarbon group and the like. Specifically, for example, monovalent groups such as an alkyl group, an alkenyl group, an alkynyl group, a cycloalkyl group, an aryl group, an aralkyl group and the like, and divalent groups derived therefrom are used. As "alkyl group", "alkenyl group", "alkynyl group", "cycloalkyl group", "aryl group", or "aralkyl group" as the moiety other than "aliphatic hydrocarbon group", those similar to the aforementioned groups can be mentioned. The "hydrocarbon group" is optionally substituted by a substituent selected from a halogen atom (chlorine atom, bromine atom, fluorine atom, iodine atom), a $C_{1-6}$ alkyl group optionally substituted by one or more halogen atoms, an oxo group and the like.

The "organic group having an alkyl group having not less than 10 and not more than 300 carbon atoms and/or an alkenyl group having not less than 10 and not more than 300 carbon atoms" indicated as "$R^5$ (group)" and/or "$R^7$ (group)" constituting Z in the above-mentioned formula (I) may contain plural "alkyl groups having not less than 10 and not more than 300 carbon atoms and/or alkenyl groups having not less than 10 and not more than 300 carbon atoms" due to branching and the like. When a plurality of "alkyl group having not less than 10 and not more than 300 carbon atoms and/or alkenyl group having not less than 10 and not more than 300 carbon atoms" is present in the "organic group having an alkyl group having not less than 10 and not more than 300 carbon atoms and/or an alkenyl group having not less than 10 and not more than 300 carbon atoms", they may be the same or different.

The lower limit of the total carbon number of the "organic group having an alkyl group having not less than 10 m and not more than 300 carbon atoms and/or an alkenyl group having not less than 10 and not more than 300 carbon atoms" for "$R^5$ (group)" and/or "$R^7$ (group)" constituting Z in the above-mentioned formula (I) is preferably 10 or more, more preferably 12 or more, further preferably 14 or more, still more preferably 18 or more, and particularly preferably 30 or more. On the other hand, the upper limit of the total carbon number of the "organic group having a an alkyl group having not less than 10 and not more than 300 carbon atoms and/or an alkenyl group having not less than 10 and not more than 300 carbon atoms" for "$R^5$(group)" and/or "$R^7$(group)" is preferably 200 or less, more preferably 150 or less, further preferably 120 or less, still more preferably 100 or less, especially preferably 80 or less, and particularly preferably 60 or less. When the carbon number is higher, the solubility of the compound of the present invention in a polar solvent is fine even when the morpholino oligonucleotide has a long chain.

A preferable embodiment of Z represented by the above-mentioned formula (a2) is a group represented by the formula (a2), wherein, in the formula (a2), ring A is a benzene ring;
$R_a$ and $R_b$ are both hydrogen atoms;
$R^4$ is a hydrogen atom,
Q in the number of k is —O—,
$R^5$ in the number of k are each independently an organic group having an alkyl group having not less than 10 and not more than 300 carbon atoms and/or an alkenyl group having not less than 10 and not more than 300 carbon atoms (e.g., 010-40 alkyl group); and
k is an integer of 1 to 3.

Another preferable embodiment of Z represented by the above-mentioned formula (a2) is a group wherein, in the formula (a2), ring A is a benzene ring;
k is an integer of 1-3;
$R_a$ and $R_b$ are both hydrogen atoms;
$R^4$ is a hydrogen atom,
Q in the number of k is —O—,
$R^5$ in the number of k are each independently a benzyl group having 1 to 3 alkyl groups having not less than 10 and not more than 300 carbon atoms and/or alkenyl groups having not less than 10 and not more than 300 carbon atoms, or a cyclohexyl group having 1 to 3 alkyl groups having not less than 10 and not more than 300 carbon atoms and/or alkenyl groups having not less than 10 and not more than 300 carbon atoms; and ring A optionally further has, in addition to QR$^5$ in the number of k, substituent(s) selected from the group consisting of a halogen atom, a $C_{1-6}$ alkyl group optionally substituted by a halogen atom, and a $C_{1-6}$ alkoxy group optionally substituted by a halogen atom.

Another preferable embodiment of Z represented by the above-mentioned formula (a2) is a group wherein, in the formula (a2),
ring A is a benzene ring;
$R_a$ is a hydrogen atom; and
$R^4$ is a hydrogen atom;
$R_b$ is a group represented by the above-mentioned formula (a3) (wherein * indicates a bonding position; ring B is a benzene ring; j is an integer of 0 to 3; Q in the number of j is —O—; $R^7$ in the number of j are each independently a $C_{10-40}$ alkyl group; and $R^6$ is a hydrogen atom.

A still another preferable embodiment of Z represented by the above-mentioned formula (a2) is a group wherein, in the formula (a2),
ring A is a benzene ring;
$R_a$ is a hydrogen atom;
$R_b$ is a group represented by the above-mentioned formula (a3) (wherein * indicates a bonding position; ring B is a benzene ring; j is an integer of 0 to 3; Q in the number of j is —O—; $R^7$ in the number of j are each independently a $C_{10-40}$ alkyl group;
$R^6$ is joined with $R^4$ of ring A to form a single bond or —O—, and whereby, ring A and ring B are joined to form a fluorenyl group or a xanthenyl group.

Another preferable embodiment of Z represented by the above-mentioned formula (a2) is a group wherein, in the formula (a2),
ring A is a benzene ring;
$R_a$ and $R_b$ are joined to form an oxygen atom;
$R^4$ is a hydrogen atom,
Q in the number of k is —O—,
$R^5$ in the number of k are each independently an organic group having an alkyl group having not less than 10 and not more than 300 carbon atoms and/or an alkenyl group having not less than 10 and not more than 300 carbon atoms (e.g., 010-40 alkyl group); and
k is an integer of 1 to 3.

Another preferable embodiment of Z represented by the above-mentioned formula (a2) is a group wherein, in the formula (a2),
ring A is a benzene ring;
k is an integer of 1 to 3;
$R_a$ and $R_b$ are joined to form an oxygen atom;
$R^4$ is a hydrogen atom;
Q in the number of k is —O—,
$R^5$ in the number of k are each independently a benzyl group having 1 to 3 alkyl groups having not less than 10 and not more than 300 carbon atoms and/or alkenyl groups having not less than 10 and not more than 300 carbon atoms, or a cyclohexyl group having 1 to 3 alkyl groups having not less than 10 and not more than 300 carbon atoms and/or alkenyl groups having not less than 10 and not more than 300 carbon atoms; and
ring A optionally further has, in addition to QR$^5$ in the number of k, substituent(s) selected from the group consisting of a halogen atom, a $C_{1-6}$ alkyl group optionally substituted by a halogen atom(s), and a $C_{1-6}$ alkoxy group optionally substituted by a halogen atom(s).

As the protecting group represented by the formula (II): Z—Y-L-, a group not easily cleaved under acidic conditions under which the protecting group P$^1$ of the morpholine ring nitrogen atom at the 3'-terminus can be removed, and cleaved under basic conditions is preferable.

Representative examples of the protecting group include a group wherein, for example,
L is a group represented by the above-mentioned formula (a1) (preferably a succinyl group etc.), and
Z—Y is the following group:
a 3,4,5-tri(octadecyloxy)benzyloxy group,
a 3,5-di(docosyloxy)benzyloxy group,
a 3,5-bis[3',4',5'-tri(octadecyloxy)benzyloxy]benzyloxy group,
a 3,4,5-tris[3',4',5'-tri(octadecyloxy)benzyloxy]benzyloxy group,
a 3,4,5-tri(octadecyloxy)benzylamino group,
a 2,4-di(docosyloxy)benzylamino group,
a 3,5-di(docosyloxy)benzylamino group,
a di(4-docosyloxyphenyl)methylamino group,
a 4-methoxy-2-[3',4',5'-tri(octadecyloxy)benzyloxy]-benzylamino group,
a 4-methoxy-2-[3',4',5'-tri(octadecyloxy)cyclohexylmethyloxy]benzylamino group,
a 2,4-di(dodecyloxy)benzylamino group,
a phenyl(2,3,4-tri(octadecyloxy)phenyl)methylamino group,
a di[4-(12-docosyloxydodecyloxy)phenyl]methylamino group,
a 3,5-bis[3',4',5'-tri(octadecyloxy)benzyloxy]benzylamino group, or
a 3,4,5-tris[3',4',5'-tri(octadecyloxy)benzyloxy]-benzylamino group.

In another representative example of the protecting group, L is a single bond, and Z—Y— is the following group:
3,4,5-tri(octadecyloxy)benzoyl group, or
3,4,5-tri(2',3'-dihydrophytyloxy)benzoyl group.

As another embodiment of the protecting group Z—Y-L-, the following benzylsuccinyl groups and diphenylmethylsuccinyl groups can be mentioned.
a 2-{2,4-di(2',3'-dihydrophytyloxy)benzylaminocarbonyl}-ethylcarbonyl group;
a 3,5-di(2',3'-dihydrophytyloxy)benzylsuccinyl group;
a 4-(2',3'-dihydrophytyloxy)benzylsuccinyl group;
a 2-{1-[(2-chloro-5-(2',3'-dihydrophytyloxy)phenyl)]-benzylaminocarbonyl}ethylcarbonyl group;
a 3,4,5-tri(2',3'-dihydrophytyloxy)benzylsuccinyl group;
a 2-{3,4,5-tri(2',3'-dihydrophytyloxy)benzylaminocarbonyl}ethylcarbonyl group;
a 2-{4-(2',3'-dihydrophytyloxy)benzylaminocarbonyl}ethylcarbonyl group;
a 2-{2-[3',4',5'-tri(2",3"-dihydrophytyloxy)benzyloxy]-4-methoxybenzylaminocarbonyl}ethylcarbonyl group;
a 2-{4-(2',3'-dihydrophytyloxy)-2-methoxybenzylaminocarbonyl}ethylcarbonyl group;
a 4-(2',3'-dihydrophytyloxy)-2-methylbenzylsuccinyl group;
a 2-{4-(2',3'-dihydrophytyloxy)-2-methylbenzylaminocarbonyl}ethylcarbonyl group;
a 4-[2,2,4,8,10,10-hexamethyl-5-dodecanoylamino]-benzylsuccinyl group;
a 2-{4-[2,2,4,8,10,10-hexamethyl-5-dodecanoylamino]-benzylaminocarbonyl}ethylcarbonyl group;
a 4-(3,7,11-trimethyldodecyloxy)benzylsuccinyl group;
a 2-{4-(3,7,11-trimethyldodecyloxy)benzylaminocarbonyl}ethylcarbonyl group;
a 2-{3, 5-di(2',3'-dihydrophytyloxy)benzylaminocarbonyl}-ethylcarbonyl group;
a 2-{1-[2,3,4-tri(2',3'-dihydrophytyloxy)phenyl]benzylaminocarbonyl}ethylcarbonyl group;

a 2-{1-[4-(2',3'-dihydrophytyloxy)phenyl]-4'-(2',3'-dihydrophytyloxy)benzylaminocarbonyl}ethylcarbonyl group;

a 3,4,5-tris[3,4,5-tri(2',3'-dihydrophytyloxy)-benzyl]benzylsuccinyl group; and a 2-{3,4,5-tris[3,4,5-tri(2',3'-dihydrophytyloxy)benzyl]-benzylaminocarbonyl}ethylcarbonyl group.

Another preferable embodiment of the protecting group represented by the formula (II): Z—Y-L- is a group wherein
L and Y are each a single bond,
Z shows the formula (a2),
ring A is a benzene ring;
$R_a$ and $R_b$ are joined to form an oxygen atom;
$R^4$ is a hydrogen atom,
Q in the number of k is —O—,
$R^5$ in the number of k are each independently an organic group having an alkyl group having not less than 10 and not more than 300 carbon atoms and/or an alkenyl group having not less than 10 and not more than 300 carbon atoms (e.g., $C_{10-40}$ alkyl group); and
k is an integer of 1 to 3.

Another preferable embodiment of the protecting group represented by the formula (II): Z—Y-L- is a group wherein
L shows the formula (a1),
$L_2$ is *N($R^3$)—$R^1$—N($R^2$)C(=O) (wherein  indicates the bonding position to $L^1$, * indicates the bonding position to Y,
$R^1$ is an optionally substituted $C_{1-22}$ alkylene group, $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond),
Y is a single bond,
Z shows the formula (a2),
ring A is a benzene ring;
$R_a$ and $R_b$ are joined to form an oxygen atom;
$R^4$ is a hydrogen atom,
Q in the number of k is —O—,
$R^5$ in the number of k are each independently an organic group having an alkyl group having not less than 10 and not more than 300 carbon atoms and/or an alkenyl group having not less than 10 and not more than 300 carbon atoms (e.g., $C_{10-40}$ alkyl group); and
k is an integer of 1 to 3.

A preferable embodiment of the compound of the present invention represented by the formula (I) is a compound of the formula (I), wherein
m is 0,
$P^1$ is a trityl group, a di($C_{1-6}$ alkoxy)trityl group or a mono($C_{1-6}$ alkoxy)trityl group;
$P^2$ is a tert-butyldimethylsilyl group, a diisopropylphenylsilyl group, triphenylsilyl group or a diphenyl tert-butoxy silyl group;
Base$^1$ is a cytosyl group, a uracil group, a thyminyl group, an adenyl group, or a guanyl group, each of which is optionally protected; and
Base$^2$ is a cytosyl group, a uracil group, a thyminyl group, an adenyl group, or a guanyl group, each of which is optionally protected.

Production Method of the Compound of the Present Invention.

A production method of the compound of the present invention represented by the formula (I) wherein m is 0 (hereinafter to be referred to as "the formula (Ia)") is not particularly limited, and it can be produced by a method known per se (Richard T. Pon et al., Nucleic Acids Research 2004, 32, 623-631, which is incorporated herein by reference in its entirety) or a method analogous thereto.

A general production method of a compound of the above-mentioned formula (Ia) wherein $P^2$ is the formula (II) Z—Y-L- (wherein L is a succinyl group, and Y and Z are as described above) is shown below.

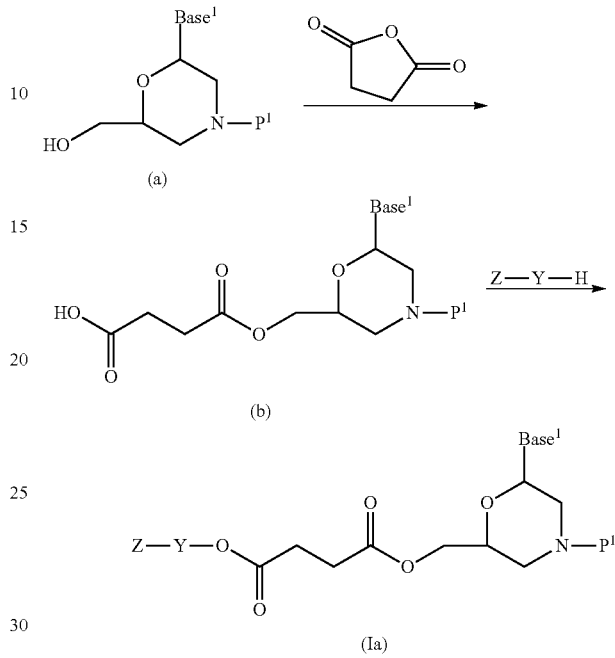

wherein each symbol is as defined above.

Morpholino nucleoside (a) wherein the 3'-terminus morpholine ring nitrogen atom is protected by a protecting group $P^1$ is reacted with succinic anhydride in the presence of a base to give compound (b) wherein succinic acid is introduced into the 5'-hydroxy group. Compound (b) is subjected to a dehydration condensation with a precursor (Z—Y—H) (alcohol or amine) of the protecting group in the presence of a condensing agent, whereby a compound represented by the formula (Ia) can be obtained.

The conversion step of the above-mentioned morpholino nucleoside (a) to compound (b) is advantageously performed in a solvent inert to the reaction. While such solvent is not particularly limited as long as the reaction proceeds, halogenated hydrocarbon solvents such as dichloromethane, 1,2-dichloroethane, chloroform, carbon tetrachloride and the like, aromatic hydrocarbon solvents such as benzene, toluene, xylene and the like, aliphatic hydrocarbon solvents such as pentane, hexane, heptane, octane and the like, ether solvents such as diethyl ether, tetrahydrofuran, cyclopentyl methyl ether and the like, and mixed solvents thereof are preferable. Of these, dichloromethane and chloroform are particularly preferable.

While the base is not particularly limited, for example, an organic base mentioned below can be used, with preference given to N,N-dimethylaminopyridine, triethylamine and the like.

The above-mentioned dehydration condensation step is advantageously performed in a solvent inert to the reaction. While such solvent is not particularly limited as long as the reaction proceeds, halogenated hydrocarbon solvents such as dichloromethane, 1,2-dichloroethane, chloroform, carbon tetrachloride and the like, aromatic hydrocarbon solvents such as benzene, toluene, xylene and the like, or aliphatic hydrocarbon solvents such as pentane, hexane, heptane, octane and the like, and mixed solvents thereof are preferable. Of these, dichloromethane and chloroform are particularly preferable.

Examples of the condensing agent used for the condensation reaction of compound (b) with Z—Y—H include dicyclohexylcarbodiimide (DCC), diisopropylcarbodiimide (DIC), N-ethyl-N'-(3-dimethylaminopropyl)carbodiimide and hydrochloride thereof (EDC HCl), (benzotriazol-1-yloxy)tripyrrolidinophosphonium hexafluorophosphate (Py-Bop), O-(benzotriazol-1-yl)-N,N,N',N'-tetramethyluronium tetrafluoroborate (TBTU), 1-[bis(dimethylamino)methylene]-5-chloro-1H-benzotriazolium-3-oxide hexafluorophosphate (HCTU), O-benzotriazole-N,N,N',N'-tetramethyluronium hexafluorophosphate (HBTU) and the like. Of these, HBTU, HCTU, N-ethyl-N'-(3-dimethylaminopropyl)carbodiimide and hydrochloride thereof (EDC HCl) are preferable.

The amount of the condensing agent to be used is 1 to 10 mol, preferably 1 to 5 mol, per 1 mol of compound (b). The amount of Z—Y—H to be used is 1 to 10 mol, preferably 1 to 5 mol, per 1 mol of compound (b). While the reaction temperature is not particularly limited as long as the reaction proceeds, it is preferably −10° C. to 50° C., more preferably 0° C. to 30° C. The reaction time is 30 min to 70 hours.

A compound of the above-mentioned formula (Ia) wherein L is other than a succinyl group can also be produced by performing a reaction similar to the above-mentioned production method except that a corresponding acid anhydride, a corresponding dicarboxylic acid halide, an activated ester of corresponding dicarboxylic acid or the like is used instead of succinic anhydride.

A compound wherein Y is a single bond can be produced by reacting an activated derivative (halide, acid halide, activated carboxy group etc.) of Z—Y—H with morpholino nucleoside (a) by a method known per se, or reacting Z—Y—H with morpholino nucleoside (a) in the presence of a condensing agent. The condensation reaction of Z—Y—H and morpholino nucleoside (a) can be performed in the same manner as in the condensation reaction of Z—Y—H and compound (b).

A compound of the above-mentioned formula (I) wherein m is one or more can be produced by repeating the 5'-terminus elongation process according to the following production method of the present invention and using a compound represented by the formula (Ia) as a starting material.

While the production method of precursor (Z—Y—H) (alcohol, amine or carboxylic acid) of the aforementioned protecting group is not particularly limited, it can be produced from a starting compound according to a method known per se (e.g., Bull. Chem. Soc. Jpn. 2001, 74, 733-738, JP-A-2000-44493, WO 2006/104166, WO 2007/034812, WO 2007/122847, WO 2010/113939, JP-A-2010-275254, WO 2012/157723 etc., all of which are incorporated herein by reference in their entireties) or a method analogous thereto.

A compound to be used as a starting compound, for example, a halide corresponding to $R^5$ and $R^7$ constituting Z in the formula (I) and the like is a commercially available product, or can be produced according to a method known per se or a method analogous thereto.

Also, the precursor (Z—Y—H) of the protecting group can be produced by a method known per se or a method analogous thereto. When a starting compound has a substituent (e.g., a hydroxy group, amino group, a carboxy group) that influences the reaction, the starting compound is generally protected in advance by a suitable protecting group according to a known method and then subjected to the reaction. Such protecting group can be removed after the reaction by a known method such as an acid treatment, an alkali treatment, a catalytic reduction and the like.

While the production method of morpholino nucleoside (a) wherein the 3'-terminus morpholine ring nitrogen atom is protected by protecting group $P^1$ is not particularly limited, it can be produced from morpholino nucleoside (1) by a method known per se (e.g., see WO 91/09033A1 which is incorporated herein by reference in its entirety) or a method analogous thereto.

For example, when $P^1$ is a trityl group, morpholino nucleoside (1) is reacted with trityl chloride in the presence of a base such as triethylamine and the like, whereby compound (a) can be obtained.

Also, compound (a) wherein $P^1$ is a hydrogen atom can be obtained by subjecting compound (a) wherein $P^1$ is a temporary protecting group to the below-mentioned deprotection step (1).

Production Method of the Present Invention.

The production method of the morpholino oligonucleotide of the present invention (hereinafter to be also referred to as the "production method of the present invention") is explained. Specifically, a production method from appropriately protected n-mer morpholino oligonucleotide to appropriately protected n+p-mer morpholino oligonucleotide is explained. For example, when n=1, n-mer morpholino oligonucleotide is to be understood as "morpholino nucleoside", and when p=1, p-mer morpholino oligonucleotide is to be understood as "morpholino nucleoside" and n+p-mer morpholino oligonucleotide is to be understood as "dinucleotide".

The production method of the present invention comprises the following step (2).

(2) A step of condensing a p-mer morpholino oligonucleotide (p is any integer of one or more), wherein a 5'-hydroxy group is activated phosphoramidated, and a morpholine ring nitrogen atom is protected by a temporary protecting group removable under acidic conditions, with an n-mer morpholino oligonucleotide (n is any integer of one or more) wherein 5'-terminus (5'-position hydroxyl group or, when the 5'-hydroxy group has a substituent having a hydroxy group, hydroxyl group present on the substituent) and/or a nucleic acid base are/is each independently protected by a protecting group having an alkyl group having not less than 10 and not more than 300 carbon atoms and/or an alkenyl group having not less than 10 and not more than 300 carbon atoms or a protecting group removable under conditions different from those for the aforementioned temporary protecting group of the morpholine ring nitrogen atom, and the morpholine ring nitrogen atom is not protected, by a phosphoramidate bond or phosphorodiamidate bond via the morpholine ring nitrogen atom, and subjecting the obtained reaction mixture to an extraction operation to separate the n+p-mer morpholino oligonucleotide as a resultant product to the organic layer side.

The nucleic acid bases of the p-mer morpholino oligonucleotide may be each independently protected by a protecting group having an alkyl group having not less than 10 and not more than 300 carbon atoms and/or an alkenyl group having not less than 10 and not more than 300 carbon atoms or a protecting group removable under conditions different from those for the aforementioned protecting group of the morpholine ring nitrogen atom.

While the upper limit of n is not particularly limited, it is preferably not more than 50, more preferably not more than 30, further preferably not more than 20.

While the upper limit of p is not particularly limited, it is preferably not more than 50, more preferably not more than 30, further preferably not more than 20, still further preferably not more than 5, particularly preferably not more than 3.

The production method of the present invention preferably further comprises the following step (1), wherein an n-mer morpholino oligonucleotide to be used in step (2) is prepared. (1) A step of removing, before step (2) and in a non-polar solvent, the temporary protecting group of the morpholine ring nitrogen atom from the n-mer morpholino oligonucleotide wherein the morpholine ring nitrogen atom is protected by a temporary protecting group removable under acidic conditions, and 5'-terminus (5'-position hydroxyl group or, when the 5'-hydroxy group has a substituent having a hydroxy group, hydroxyl group present on the substituent) and/or the nucleic acid base are/is each independently protected by a protecting group having an alkyl group having not less than 10 and not more than 300 carbon atoms and/or an alkenyl group having not less than 10 and not more than 300 carbon atoms or a protecting group removable under conditions different from those for the aforementioned protecting group of the morpholine ring nitrogen atom, and subjecting the obtained reaction mixture to an extraction operation to separate the n-mer morpholino oligonucleotide as a resultant product to the organic layer side.

Since at least one of a 5'-position hydroxyl group or a hydroxyl group present on the substituent of 5'-position hydroxyl group and each nucleic acid base of an n-mer morpholino oligonucleotide, and each nucleic acid base of a p-mer morpholino oligonucleotide is protected by a protecting group having an alkyl group having not less than 10 and not more than 300 carbon atoms and/or an alkenyl group having not less than 10 and not more than 300 carbon atoms, the liposolubility of the obtained n+p-mer morpholino oligonucleotide is improved and the n+p-mer morpholino oligonucleotide can be purified conveniently and effectively by removing excess starting materials and by-products.

From the aspects of purification efficiency, at least one of the nucleic acid bases possessed by a p-mer morpholino oligonucleotide and an n-mer morpholino oligonucleotide is preferably protected by a protecting group having an alkyl group having not less than 10 and not more than 300 carbon atoms and/or an alkenyl group having not less than 10 and not more than 300 carbon atoms.

From the aspects of purification efficiency, the protecting group having an alkyl group having not less than 10 and not more than 300 carbon atoms and/or an alkenyl group having not less than 10 and not more than 300 carbon atoms is preferably a protecting group having a branched chain alkyl group having not less than 10 and not more than 300 carbon atoms and/or a branched chain alkenyl group having not less than 10 and not more than 300 carbon atoms.

Morpholino oligonucleotide can be isolated and produced by further including step (4) in the production method of the present invention:

(4) A step of removing all the protecting groups of the obtained n+p-mer morpholino oligonucleotide.

Each step is explained in detail in the following.

1. Explanation of "n-Mer Morpholino Oligonucleotide"

First, n-mer morpholino oligonucleotide used as a starting material of steps (1) and (2) is explained.

The n-mer morpholino oligonucleotide used in step (1) is, for example, n-mer morpholino oligonucleotide wherein the morpholine ring nitrogen atom is protected by a temporary protecting group removable under acidic conditions, as shown by, for example, the following formula (i), and the n-mer morpholino oligonucleotide used in step (2) is, for example, n-mer morpholino oligonucleotide wherein the morpholine ring nitrogen atom is not protected, as shown by, for example, the following formula (ii).

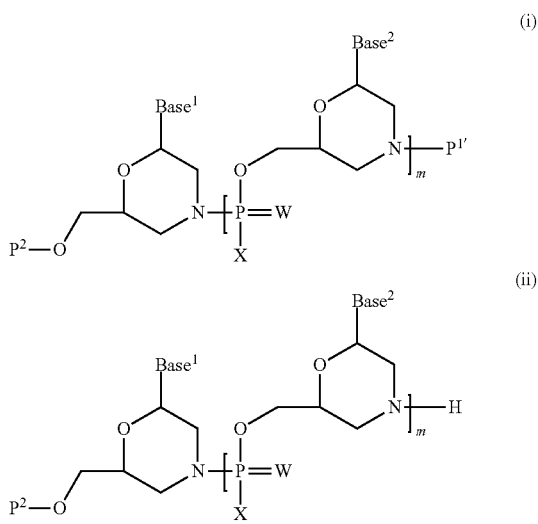

wherein
m is any integer of not less than 0 which corresponds to n−1,
$P^{1'}$ is a temporary protecting group removable under acidic conditions, and
other symbols are the same as respective definitions in the formula (I).

Each symbol in the formulas (i) and (ii) is explained below.

While the upper limit of m is not particularly limited, it is generally not more than 99, preferably not more than 74, more preferably not more than 49, further preferably not more than 29.

The temporary protecting group removable under acidic conditions for $P^{1'}$ in the formula (i) is not particularly limited as long as it can be deprotected under acidic conditions and can be used as a hydroxy-protecting group. Examples thereof include a trityl group, a 9-(9-phenyl)xanthenyl group, a 9-phenylthioxanthenyl group, di($C_{1-6}$ alkoxy)trityl groups such as a 1,1-bis(4-methoxyphenyl)-1-phenylmethyl group, a dimethoxytrityl group and the like, mono($C_{1-18}$ alkoxy)trityl groups such as 1-(4-methoxyphenyl)-1,1-diphenylmethyl group, monomethoxytrityl group and the like, and the like can be mentioned. Among these, a trityl group, a monomethoxytrityl group and a dimethoxytrityl group are preferable, and a trityl group and a dimethoxytrityl group are more preferable, in view of easiness of deprotection and easy availability.

2. Explanation of "p-Mer Morpholino Oligonucleotide"

First, p-mer morpholino oligonucleotide used as a starting material of step (2) is explained.

The "p-mer morpholino oligonucleotide (p is any integer of one or more) wherein a 5'-hydroxy group is activated phosphoramidated, and a morpholine ring nitrogen atom is protected by a temporary protecting group removable under acidic conditions" used in step (2) is not particularly limited as long as the structural requirements are met.

The "5'-hydroxy group is activated phosphoramidated" means that 5'-hydroxy group of the morpholino oligonucleotide is, for example, modified by a group represented by the following formula (c):

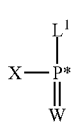
(c)

wherein

\* indicates the bonding position to the 5'-terminus hydroxyl group of morpholino oligonucleotide, $L^1$ is a leaving group, X is a di-$C_{1-6}$ alkylamino group, or a 1-piperazinyl group wherein the 4-position nitrogen atom is protected by a protecting group and optionally further substituted, and W is an oxygen atom.

The "activated phosphoramidated" means the above-mentioned formula wherein X is a di-$C_{1-6}$ alkylamino group or a 1-piperazinyl group wherein the 4-position nitrogen atom is protected by a protecting group and optionally further substituted, and W is an oxygen atom.

Examples of the leaving group for $L^1$ include a halogen atom, a methanesulfonyloxy group, a p-toluenesulfonyloxy group and the like, and a chlorine atom is preferable.

The definitions, examples and preferable embodiments of X and W are as explained for the above-mentioned formula (I).

The definitions, examples and preferable embodiments of the "temporary protecting group removable under acidic conditions" are as explained for the above-mentioned formula (I).

As a preferable p-mer morpholino oligonucleotide used in step (2), a compound represented by the formula (iii) can be mentioned.

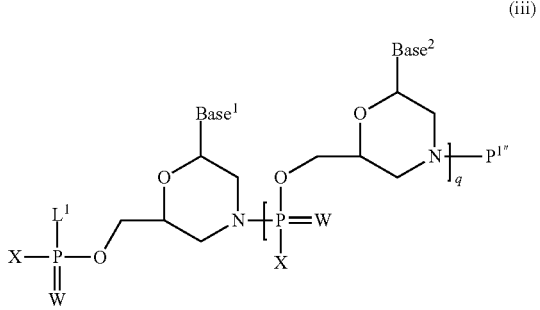
(iii)

wherein q is any integer of not less than 0 which corresponds to p-1, $P^{1''}$ is a temporary protecting group removable under acidic conditions, and other symbols are the same as respective definitions in the formula (I) and the formula (c)).

q in the formula (iii) is preferably 0. While the upper limit of q is not particularly limited, it is generally not more than 99, preferably not more than 74, more preferably not more than 49, further preferably not more than 29.

The temporary protecting group removable under acidic conditions for $P^{1''}$ in the formula (iii) is not particularly limited as long as it can be deprotected under acidic conditions and can be used as a hydroxy-protecting group. Examples thereof include a trityl group, a 9-(9-phenyl) xanthenyl group, a 9-phenylthioxanthenyl group, di($C_{1-6}$ alkoxy)trityl groups such as a 1,1-bis(4-methoxyphenyl)-1-phenylmethyl group, dimethoxytrityl and the like, mono($C_{1-18}$ alkoxy)trityl groups such as 1-(4-methoxyphenyl)-1,1-diphenylmethyl group, monomethoxytrityl group and the like, and the like can be mentioned. Among these, a trityl group, a monomethoxytrityl group and a dimethoxytrityl group are preferable, and a trityl group and a dimethoxytrityl group are more preferable, in view of easiness of deprotection and easy availability.

Preferable embodiments of other symbols in the formula (iii) are as explained for the above-mentioned formulas (I) and (c).

The p-mer morpholino oligonucleotide of the present invention can be prepared by a method known per se (e.g., the method described in WO 91/09033A1, which is incorporated herein by reference in its entirety), or a method analogous thereto. For example, a compound wherein $L^1$ is a chlorine atom can be produced by reacting a compound of the following formula (iii') which is a compound represented by the formula (iii), wherein the 5'-hydroxy group is not activated, with, for example, dichlorophosphoramidate represented by the formula (d): $Cl_2P(=W)(X)$ (wherein W and X are as defined above).

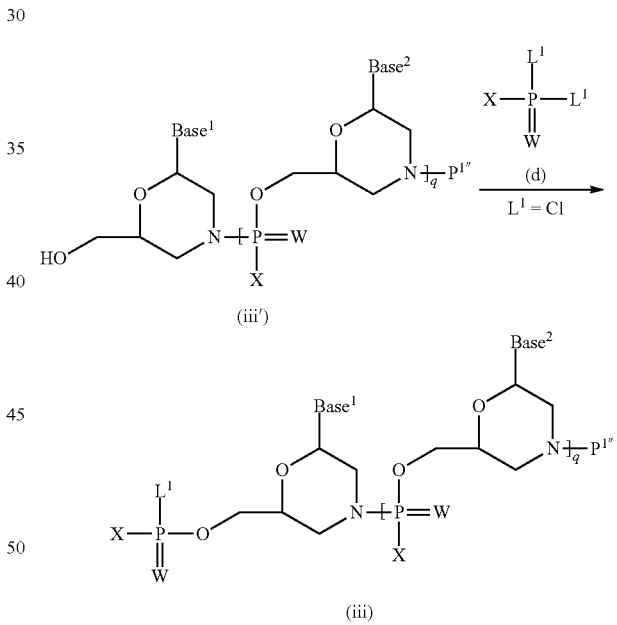
(iii')
(iii)

As dichlorophosphoramidate represented by the formula (d), a commercially available product can be used, or can be produced by a known method (e.g., the methods described in WO 91/09033, WO 2008/008113 etc., which are incorporated herein by reference in their entireties) or a method analogous thereto.

A compound of the formula (iii') can be prepared by a known method, for example, WO 91/09033, which is incorporated herein by reference in its entirety, and the like.

3. Explanation of Steps (1) to (3)

While steps (1) to (3) are explained below by reference to the formulas (i), (ii), (iii) and the like for convenience, they are not limited thereby.

Step (1) (Deprotection Step)

This step includes a step of removing, before condensation step (2) and in a non-polar solvent, the temporary protecting group of the morpholine ring nitrogen atom from the n-mer morpholino oligonucleotide (i) wherein the morpholine ring nitrogen atom is protected by a temporary protecting group removable under acidic conditions, and 5'-terminus (5'-position hydroxyl group or, when the 5'-hydroxy group has a substituent having a hydroxy group, hydroxyl group present on the substituent) and/or the nucleic acid base are/is protected by a protecting group having an alkyl group having not less than 10 and not more than 300 carbon atoms and/or an alkenyl group having not less than 10 and not more than 300 carbon atoms or a protecting group removable under conditions different from those for the aforementioned protecting group of the morpholine ring nitrogen atom, and subjecting the obtained reaction mixture to an extraction operation to separate, to the organic layer side, the n-mer morpholino oligonucleotide (ii) as a resultant product wherein 5'-terminus (5'-position hydroxyl group or hydroxyl group present on the substituent of 5'-position hydroxyl group) and/or the nucleic acid base are/is protected by a protecting group having an alkyl group having not less than 10 and not more than 300 carbon atoms and/or an alkenyl group having not less than 10 and not more than 300 carbon atoms or a protecting group removable under conditions different from those for the aforementioned protecting group of the morpholine ring nitrogen atom, and the morpholine ring nitrogen atom is not protected (deprotection step).

The above-mentioned removal of the temporary protecting group is preferably performed by reacting with an acid in the presence of a cation scavenger.

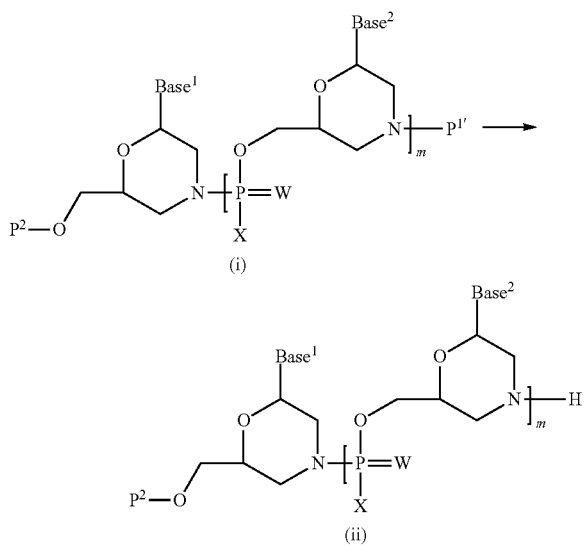

wherein each symbol is as defined above.

This step is performed in a solvent that does not influence the reaction. Since a higher solubility in the solvent is expected to afford superior reactivity, a non-polar solvent showing high solubility of n-mer morpholino oligonucleotide (i) of the present invention is preferably selected. Specifically, examples thereof include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like. Among them, dichloromethane, chloroform, 1,2-dichloroethane, benzene, toluene, xylene, mesitylene, hexane, pentane, heptane, nonane, cyclohexane, ethyl acetate, isopropyl acetate, tert-butyl methyl ether, cyclopentyl methyl ether, and the like are preferable. Two or more kinds of these solvents may be used in a mixture in an appropriate ratio.

In this step, the concentration of n-mer morpholino oligonucleotide (i) in a solvent is not particularly limited as long as the oligonucleotide is dissolved, it is preferably 1 to 30 mass %.

While the acid to be used in this step is not particularly limited as long as good deprotection can be achieved, trifluoroacetic acid, cyanopyridine trifluoroacetate and trifluoroethanol, triethylamine trifluoroacetate, cyanoacetic acid, acetic acid, dichloroacetic acid, phosphoric acid, mesylic acid, tosic acid, hydrochloric acid and the like are preferably used.

Since reaction can be achieved smoothly, trifluoroacetic acid, cyanopyridine trifluoroacetate, triethylamine trifluoroacetate, and cyanoacetic acid are more preferable, cyanopyridine trifluoroacetate and triethylamine trifluoroacetate are further preferable, and triethylamine trifluoroacetate is particularly preferable. These acids may be diluted with the above-mentioned non-polar solvent. When the aforementioned acid is used, it may be combined with a particular base (e.g., triethylamine etc.) to appropriately adjust the acidity before use.

The amount of the acid to be used in this step is 1 to 100 mol, preferably 1 to 40 mol, per 1 mol of n-mer morpholino oligonucleotide (i).

In this step, a cation scavenger may be added to prevent side reactions due to cationized compound and the like of protecting group $P^1$ such as trityl cation and the like caused by deprotection reaction. Examples of preferable cation scavengers include a cation scavenger comprising a compound having a mercapto group and a carboxy group, and a cation scavenger comprising an indole compound having a carboxy group. Specific examples of the cation scavenger include a compound having one mercapto group and one or two carboxy groups such as thiomalic acid, 3-mercaptopropionic acid, cysteine, cisteinyl glutamic acid and the like; and an indole compound having one or two carboxy groups such as indole carboxylic acid, indole dicarboxylic acid, tryptophan, tryptophanyl glutamic acid, 1-(1H-indol-5-yl) butanedicarboxylate and the like. Of these, thiomalic acid, 3-mercaptopropionic acid, and 1-(1H-indol-5-yl) butanedicarboxylate are preferable. Two or more kinds of the cation scavengers may be used in combination.

The amount of the cation scavenger to be used can be appropriately determined in consideration of an excess amount of p-mer morpholino oligonucleotide (iii) relative to n-mer morpholino oligonucleotide (ii) (number of moles of p-mer morpholino oligonucleotide (iii)—number of moles of n-mer morpholino oligonucleotide (ii)), and is preferably 1 to 20 equivalents, more preferably 1 to 10 equivalents, relative to the excess amount (moles).

While the reaction temperature in this step is not particularly limited as long as the reaction proceeds, it is preferably −10° C. to 50° C., more preferably 0° C. to 40° C. While the reaction time varies depending on the kind of n-mer morpholino oligonucleotide to be used, the kind of acid, the kind of solvent, the reaction temperature and the like, it is 5 minutes to 24 hours.

When an acid used as a deprotecting agent is present in the condensation step of the next step, deprotection of protecting group $P^{1\prime\prime\prime}$ of p-mer morpholino oligonucleotide (iii) is induced. Therefore, a removal treatment or a neutralization treatment is necessary. To continuously perform the deprotection step and subsequent condensation step in a solution, it is preferable in this step to remove the temporary protecting group of the 3'-terminus morpholine ring nitrogen atom, neutralize the compound with an organic base or inorganic base, and remove same by an extraction operation such as washing and the like.

The organic base to be used for neutralization is not particularly limited as long as it can neutralize the abovementioned acids, and the obtained salt can function as a condensing agent. Since the reaction proceeds smoothly, N,N-diisopropylethylamine, pyridine, 4-cyanopyridine, trimethylamine, sodium carbonate and potassium carbonate are preferable, N,N-diisopropylethylamine and triethylamine are more preferable, and N,N-diisopropylethylamine is particularly preferable.

The amount of the organic base to be used in this step is 1 to 10 mol, preferably 1 to 3 mol, per 1 mol of the acid.

Step (1'): in this step, moreover, an adduct of a cationized compound of protecting group $P^1$ such as trityl cation and the like, which is generated by deprotection, with a cation scavenger is removed by transfer to the aqueous layer. That is, the obtained reaction mixture is subjected to an extraction operation, and an n-mer morpholino oligonucleotide as a resultant product is separated to the organic layer side. When a non-polar solvent is used as a reaction solvent, the extraction operation can be performed by adding water to the reaction mixture. In addition, a mixed solvent of water and a hydrophilic organic solvent may also be added. For example, a mixed solvent of a hydrophilic organic solvent such as N,N-dimethylacetamide, acetonitrile, N,N-dimethylformamide and the like and water is preferably used, and a mixed solvent of N,N-dimethylformamide and water is particularly preferable. The amount of water to be present in the system can be appropriately determined by those of ordinary skill in the art within the range of conventional extraction operation, according to which the amounts of water and organic solvent can be appropriately determined when using a mixed solvent thereof.

Step (2) (Condensation Step)

This step includes a step of condensing a p-mer morpholino oligonucleotide (iii) wherein a 5'-hydroxy group is activated phosphoramidated, and a morpholine ring nitrogen atom is protected by a temporary protecting group removable under acidic conditions, with an n-mer morpholino oligonucleotide (ii) wherein 5'-terminus (5'-position hydroxyl group or, when the 5'-hydroxy group has a substituent having a hydroxy group, hydroxyl group present on the substituent) and/or a nucleic acid base are/is protected by a protecting group having an alkyl group having not less than 10 and not more than 300 carbon atoms and/or an alkenyl group having not less than 10 and not more than 300 carbon atoms or a protecting group removable under conditions different from those for the aforementioned temporary protecting group of the morpholine ring nitrogen atom, and the morpholine ring nitrogen atom is not protected, by a phosphoramidate bond or phosphorodiamidate bond via the morpholine ring nitrogen atom, and subjecting the obtained reaction mixture to an extraction operation to separate the n+p-mer morpholino oligonucleotide (iv) as a resultant product to the organic layer side. The obtained reaction mixture is preferably treated, before the extraction operation, with a quenching agent comprising a compound having a secondary amino group and a carboxy group.

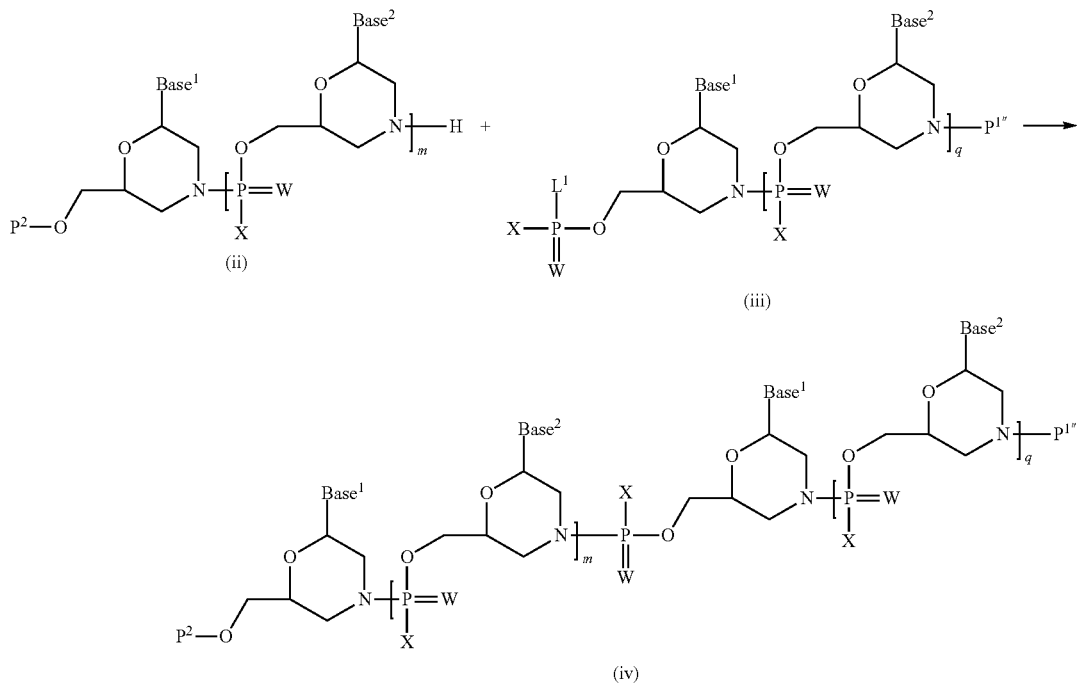

wherein each symbol is as defined above.

As the p-mer morpholino oligonucleotide (iii) wherein a 5'-hydroxy group is activated phosphoramidated, and a morpholine ring nitrogen atom is protected by a temporary protecting group removable under acidic conditions, a morpholino nucleoside wherein p is 1 (i.e., morpholino nucleoside wherein 5'-hydroxy group is activated phosphoramidated, and morpholine ring nitrogen atom is protected by temporary protecting group $P^{1''}$) is preferable.

In this step, the n-mer morpholino oligonucleotide (ii) to be used is not particularly limited, and one obtained in the aforementioned step (1) can be preferably used. In this case, a p-mer morpholino oligonucleotide (iii) only needs to be added directly to the reaction mixture after step (1), without isolating the n-mer morpholino oligonucleotide (ii).

This step is performed in a solvent that does not influence the reaction. A non-polar solvent showing high solubility of n-mer morpholino oligonucleotide (ii) of the present invention is preferably selected. Specifically, examples thereof include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like. Among them, dichloromethane, chloroform, 1,2-dichloroethane, benzene, toluene, xylene, mesitylene, hexane, pentane, heptane, nonane, cyclohexane, ethyl acetate, isopropyl acetate, tert-butyl methyl ether, cyclopentyl methyl ether, and the like are preferable. Two or more kinds of these solvents may be used in a mixture in an appropriate ratio. In addition, a polar solvent may be mixed at an appropriately ratio as long as n-mer morpholino oligonucleotide (ii) is dissolved. Specifically, polar solvents such as nitrile solvents such as acetonitrile, propionitrile and the like; ketone solvents such as acetone, 2-butanone and the like; polar ether solvents such as 1,4-dioxane, tetrahydrofuran and the like; amide solvents such as N,N-dimethylformamide, N,N-dimethylacetamide, N-methylpyrrolidone, 1,3-dimethyl-2-imidazolinone and the like, sulfoxide solvents such as dimethyl sulfoxide and the like can be mentioned.

The amount of p-mer morpholino oligonucleotide (iii) to be used is 1 to 10 mol, preferably 1 to 5 mol, more preferably 1 to 2 mol, per 1 mol of n-mer morpholino oligonucleotide (ii).

While the reaction temperature is not particularly limited as long as the reaction proceeds, 0° C. to 100° C. is preferable, and 20° C. to 50° C. is more preferable. While the reaction time varies depending on the kind of n-mer morpholino oligonucleotide (ii) and p-mer morpholino oligonucleotide (iii) to be condensed, the reaction temperature and the like, it is 30 minutes to 24 hours.

After the completion of the condensation reaction and before the extraction operation, the reaction mixture is preferably treated with a quenching agent. Using the quenching agent, p-mer morpholino oligonucleotide (iii) remaining in the condensation reaction can be completely quenched, and induction of double addition in the condensation reaction of the next cycle by the residual activated morpholino nucleotide can be avoided, which in turn prevents degradation of the quality of the objective morpholino oligonucleotide.

The double addition refers to a doubly addition of the same residue of activated morpholino nucleotide used and remained in the condensation reaction of the previous cycle, which reacts in the condensation reaction of the subsequent cycle.

As the quenching agent, a quenching agent comprising a compound having a secondary amino group and a carboxy group, or a compound having a phosphono group is preferable. As a quenching agent comprising a compound having a secondary amino group and a carboxy group, a quenching agent comprising a compound having one secondary amino group and one or two carboxy groups is preferable. As a quenching agent comprising a compound having a secondary amino group and a carboxy group, specifically, for example, prolylglutamic acid, N-methyl β-alanine, proline, N-methylglycine, N-methylglycylglutamic acid, prolylproline, prolylaspartic acid and the like can be mentioned. Of these, prolylglutamic acid and prolylproline are preferable. As a quenching agent comprising a compound having a phosphono group, a compound having a phosphono group such as phenylphosphonic acid and the like can be mentioned. Of these, phenylphosphonic acid is preferable. Two or more kinds of quenching agents may be used in combination.

The amount of the quenching agent comprising a compound having a secondary amino group and a carboxy group to be used can be appropriately determined in consideration of an excess amount of p-mer morpholino oligonucleotide (iii) relative to n-mer morpholino oligonucleotide (ii) (number of moles of p-mer morpholino oligonucleotide (iii)−number of moles of n-mer morpholino oligonucleotide (ii)), and is preferably 0.1 to 10 equivalents, more preferably 0.3 to 3 equivalents, relative to the excess amount (moles).

After adding a quenching agent comprising a compound having a secondary amino group and a carboxy group to the reaction mixture, p-mer morpholino oligonucleotide (iii) can be completely quenched by reacting the mixture at 0° C. to 100° C., preferably 20° C. to 50° C., for 30 minutes to 24 hours, preferably 30 minutes to 5 hours.

The reaction mixture treated with a quenching agent is subjected to an extraction operation, whereby impurities based on the starting monomer can be efficiently removed to the aqueous layer side by extraction operation. That is, the reaction mixture is subjected to an extraction operation, and an n+p-mer morpholino oligonucleotide as a resultant product is separated to the organic layer side. When a non-polar solvent is used as a reaction solvent, the extraction operation can be performed by adding water to the reaction mixture. In addition, a mixed solvent of water and a polar solvent may also be added. For example, a mixed solvent of a polar solvent such as N,N-dimethylacetamide, acetonitrile, N,N-dimethylformamide and the like and water is preferably used, and a mixed solvent of N,N-dimethylformamide and water is particularly preferable. The amount of water to be present in the system can be appropriately determined by those of ordinary skill in the art within the range of conventional extraction operation, according to which the amounts of water and organic solvent can be appropriately determined when using a mixed solvent thereof.

Step (3) (Extraction Isolation Step)

This step includes a method of isolating and purifying an n+p-mer morpholino oligonucleotide (iv) by an extraction operation from the reaction mixture containing the n+p-mer morpholino oligonucleotide (iv) obtained in step (2).

While the extraction operation is not particularly limited, preferably, a non-polar solvent and/or water are/is added as necessary to the reaction mixture obtained in step (2) to allow for phase separation between non-polar solvent layer-aqueous layer, and the n+p-mer morpholino oligonucleotide is transferred to the non-polar solvent. By this extraction operation, remaining impurities such as starting material, reagent, by-product (e.g., acid, quenching agent, p-mer morpholino oligonucleotide to which quenching agent is added etc.) and the like can be eliminated in the aqueous phase.

As the non-polar solvent to be added as necessary in this step for transfer of the n+p-mer polymerization oligonucleotide (iv) to the non-polar solvent, the same non-polar solvents as those used in the condensation reaction described above can be mentioned. Therefore, when a non-polar solvent is used as a solvent for the condensation reaction, it may be used as it is as a non-polar solvent for extraction. Where necessary, a polar solvent may be added and, for example, a mixed solvent of water and a polar solvent may be added to a non-polar solvent for phase separation and an extraction operation may be performed. Examples of the polar solvent to be added as necessary include alcohol solvents such as methanol, ethanol, isopropanol and the like, nitrile solvents such as acetonitrile, propionitrile and the like, ketone solvents such as acetone, 2-butanone and the like, polar ether solvents such as 1,4-dioxane, tetrahydrofuran and the like, amide solvents such as N,N-dimethylformamide, N,N-dimethylacetamide, N-methylpiperidone and the like, sulfoxide solvents such as dimethyl sulfoxide and the like, and a mixed solvent of two or more kinds thereof. Of these, amide solvents, nitrile solvents, and combination of these are preferable, N,N-dimethylacetamide, acetonitrile, N,N-dimethylformamide, and combination of these are more preferably used. As the polar solvent in the present invention, N,N-dimethylformamide is particularly preferable.

Impurities can be eliminated by removing the aqueous layer after phase separation between non-polar solvent layer-aqueous layer. Furthermore, a small amount of remaining impurities can be further eliminated by adding water or a mixed solvent of water and a polar solvent to a non-polar solvent after removal of the aqueous layer, stirring the mixture, separating the layers, and removing the aqueous layer (such extraction operation is sometimes referred to as "washing" in the present invention).

The number of washing with a polar solvent is not particularly limited, and the washing may be repeated until impurities in the non-polar solvent layer are reduced to such an extent that the subsequent cycles of nucleotide elongation reaction are not inhibited, by analyzing the non-polar solvent by thin layer silica gel chromatography, high performance liquid chromatography and the like.

While the content of water in a mixed solvent of water and a polar solvent can be appropriately set by those of ordinary skill in the art, for example, 1 to 10% (v/v) is preferable, and 3 to 8% (v/v) is more preferable.

An n+p-mer morpholino oligonucleotide (iv) can be isolated by concentrating the non-polar solvent layer after the extraction operation. In this case, nucleotide elongation can be repeated in one pot by adding solvents and reagents for the next cycle to the reaction vessel after concentration. Alternatively, the non-polar solvent layer after extraction operation and without concentration can also be subjected to the subsequent cycles of nucleotide elongation.

The production method of morpholino oligonucleotide of the present invention can afford the objective highly polymerized morpholino oligonucleotide with high purity and high yield by repeating the above-mentioned steps desired times in the order of (1) to (3).

Step (4) (Deprotection, Morpholino Oligonucleotide Isolation Step)

In the production method of morpholino oligonucleotide of the present invention, deprotection is performed after step (2) according to the kind and properties of the protecting group, whereby morpholino oligonucleotide can be isolated. All protecting groups of the morpholino oligonucleotide can be removed according to the deprotection method described in Greene's PROTECTIVE GROUPS IN ORGANIC SYNTHESIS, 4th ed., Wiley-Interscience (2006), which is incorporated herein by reference in its entirety, and the like. To be specific, a protecting group having an alkyl group having not less than 10 and not more than 300 carbon atoms and/or an alkenyl group having not less than 10 and not more than 300 carbon atoms in the present invention, as well as a protecting group removable under conditions different from those for a protecting group of the morpholine ring nitrogen atom can all be removed by a treatment with aqueous ammonia, aqueous ammonia/ethanol solution, or a mixture of aqueous ammonia and aqueous methylamine solution. In addition, the 3'-terminus protecting group of the morpholine ring nitrogen atom of the morpholino oligonucleotide can be removed by a treatment with the acid used in step (1) or an appropriately diluted solution of such acid.

The progress of the reaction in each of the above-mentioned steps can be confirmed by a method similar to conventional liquid-phase organic synthesis reaction. That is, the reaction can be traced by thin layer silica gel chromatography, high performance liquid chromatography and the like.

The morpholino oligonucleotide obtained by step (4) can also be led to a desired morpholino oligonucleotide derivative by further applying an organic synthesis reaction.

The morpholino oligonucleotide produced by the present invention can be used for various uses such as various pharmaceutical products (RNA, DNA, oligonucleic acid medicine, peptide modified morpholino oligonucleotide etc.) for human or animal, functional food, food for specified health uses, food, chemical product, polymer material for living body or industrial use, and the like.

Other features of the invention will become apparent in the course of the following descriptions of exemplary embodiments which are given for illustration of the invention and are not intended to be limiting thereof.

EXAMPLES

The reagents, apparatuses and materials used in the present invention are commercially available unless otherwise specified. In the present specification, when indicated by abbreviation, unless particularly indicated, each indication is based on the abbreviation of the IUPAC-IUB Commission on Biochemical Nomenclature or conventional abbreviations in the art. The ratios shown for mixed solvents (solutions) are volume ratios unless otherwise specified. % shows wt % unless otherwise specified.

The abbreviations used in Examples are as follows.

mo: morpholino nucleoside
moA: morpholinoadenosine
moG: morpholinoguanosine
moC: morpholinocytidine
moT: morpholinothymidine
moU: morpholinouridine
PMO: phosphorodiamidate morpholino oligonucleotide For example, indication of PMO[A-G-C] means that the left side is the 5'-terminus, the right side is the 3'-terminus, and it is a phosphorodiamidate morpholino oligonucleotide in the order of morpholinoadenosine, morpholinoguanosine, and morpholinocytidine from the 5'-terminus.

bz: benzoyl group
Bzl: benzyl group
cHx: cyclohexyl group
pac: phenoxyacetyl group
ce: 2-cyanoethyl group When a nucleic acid base of morpholino nucleoside is protected, the protecting group is indicated as superscript to the right of the abbreviation (A, G, C, T and U) of the nucleic acid base.

For example, $C^{bz}$ means that the amino group of cytosine is protected by a benzoyl group, and $G^{ce/pac}$ means that the amino group of guanine is protected by a phenoxyacetyl group, and the carbonyl group is protected by a 2-cyanoethyl group.

OPhy: 3,4,5-tri(2',3'-dihydrophytyloxy)benzyloxy group
Dpm: diphenylmethyl group
suc: succinyl group
Tr, Trt: trityl group
TBSO: tert-butyldimethylsiloxy group
TOB: 3,4,5-tri(octadecyloxy)benzoyl group
PhyTOB: 3,4,5-tri(2',3'-dihydrophytyloxy)benzoyl group Example 1: Elongation Reaction Using Substrate Having Bzl(3,4,5-OPhy)-O-Containing Anchor at 5'-Terminus

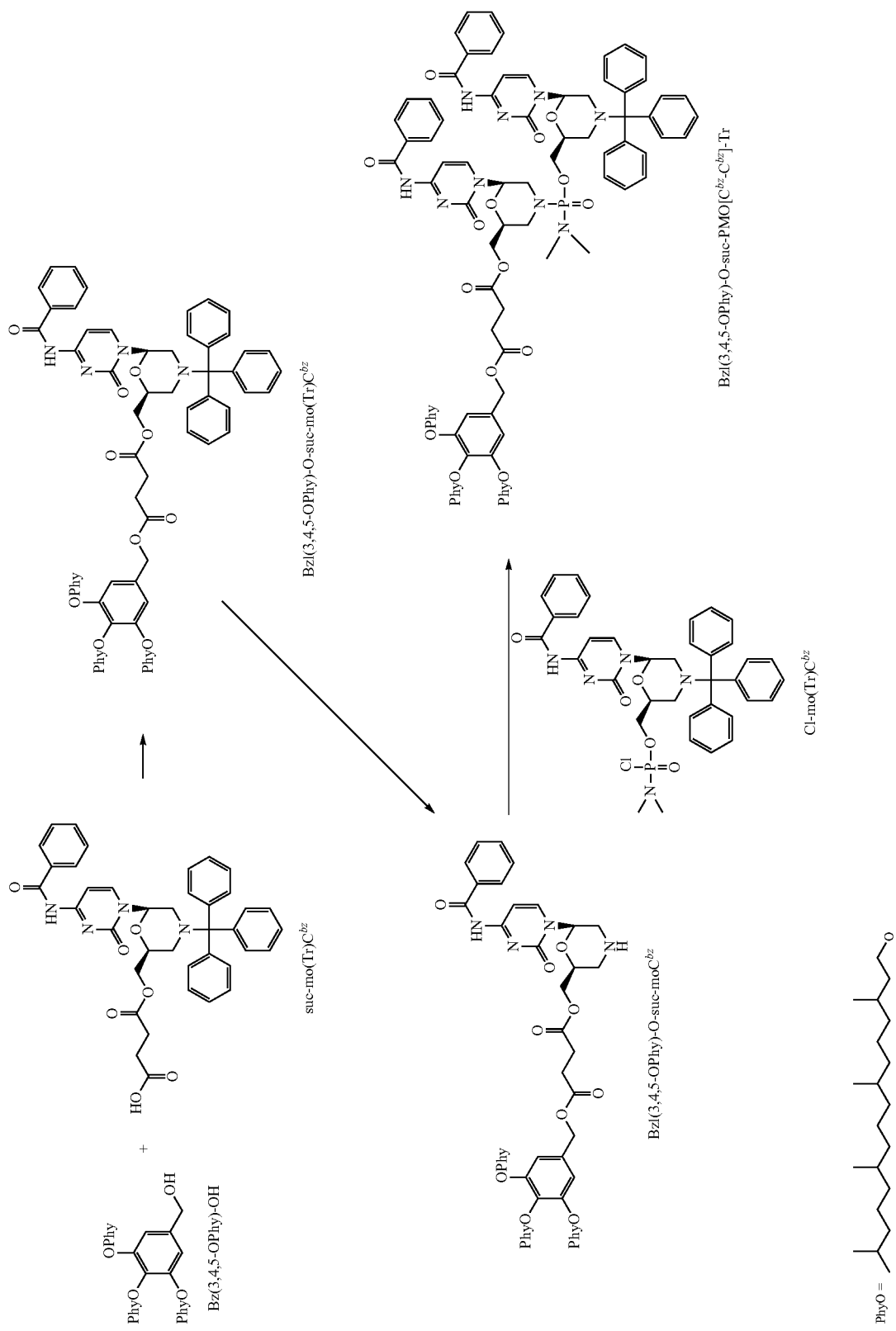

1) Condensation-1

Bzl(3,4,5-OPhy)-OH (1.00 g, 1.00 mmol) was dissolved in chloroform (10 mL), suc-mo(Tr)$C^{bz}$ (0.27 g, 0.40 mmol), 1-(3-dimethylaminopropyl)-3-ethylcarbodiimide hydrochloride (0.09 g, 0.44 mmol) and 4-dimethylaminopyridine (10 mg, 0.02 mmol) were added thereto, and the mixture was stirred at room temperature for 17 hours. The solvent was evaporated under reduced pressure, and cyclohexane (10 mL) and heptane (5 mL) were added to the residue. Acetonitrile (10 mL) was added thereto, and partition-washing was performed twice. The solvent of the upper layer was evaporated under reduced pressure, and the mixture was dried under reduced pressure to give Bzl(3,4,5-OPhy)-O-suc-mo(Tr)$C^{bz}$ as an oil (1.64 g, 99%).

TOF-MS+ (m/z) 1652.0

2) Deprotection of Trityl Group-1

Bzl(3,4,5-OPhy)-O-suc-mo(Tr)$C^{bz}$ (1.60 g, 0.97 mmol) was dissolved in chloroform (16 mL), and 2,2,2-trifluoroethanol (4.33 mL, 59.4 mmol) and thiomalic acid (1.45 g, 9.68 mmol) were added thereto. The mixture was ice-cooled, a chloroform solution (13.7 mL) of trifluoroacetic acid (0.88 g, 7.75 mmol) and triethylamine (0.48 g, 4.84 mmol) was added dropwise, and the mixture was stirred at 15° C. for 2.5 hours. Thereafter, a chloroform solution (1.0 mL) of trifluoroacetic acid (0.110 g, 0.97 mmol) was added, and the mixture was stirred for 1 hr. The reaction mixture was ice-cooled, and a chloroform solution (31 mL) of N,N-diisopropylethylamine (3.15 g, 24.2 mmol) was added dropwise. The obtained solution was washed with a mixed solution (4:1, 20 mL×2) of 5% aqueous sodium carbonate solution and N,N-dimethylformamide. The organic layer was washed successively with a mixed solution (3:2, 20 mL×5) of 20% brine and N,N-dimethylformamide, and 20% brine (20 mL) to give an organic layer containing Bzl(3,4,5-OPhy)-O-suc-mo$C^{bz}$, and the organic layer was directly subjected to the subsequent reaction.

TOF-MS+ (m/z) 1410.0.

3) Condensation-2

N,N-diisopropylethylamine (0.30 mL, 1.74 mmol) and Cl-mo-(Tr)$C^{bz}$ (1.01 g, 1.45 mmol) were added to the organic layer (85.9 g) containing Bzl(3,4,5-OPhy)-O-suc-mo$C^{bz}$ (1.37 g, corresponding to 0.97 mmol), and the mixture was stirred at room temperature for 17 hours. The reaction mixture was ice-cooled, N,N-diisopropylethylamine (0.42 mL, 2.42 mmol), prolylglutamic acid (0.59 g, 2.42 mmol) and 2,2,2-trifluoroethanol (12.7 mL, 174 mmol) were added thereto, and the mixture was stirred at room temperature for 3 hr. Furthermore, prolylglutamic acid (0.12 g, 0.48 mmol) was added thereto, and the mixture was stirred at room temperature for 30 min. The reaction mixture was washed with 5 vol % aqueous 2,2,2-trifluoroethanol solution (70 mL×3). The objective compound was re-extracted with chloroform (4 mL) from the aqueous layer, and combined with the organic layer. The obtained organic layer containing Bzl(3,4,5-OPhy)-O-suc-PMO[$C^{bz}$-$C^{bz}$]-Tr was directly subjected to the subsequent reaction.

TOF-MS+ (m/z) 2071.1

4) Deprotection of Trityl Group-2

The organic layer (80.3 g) containing Bzl(3,4,5-OPhy)-O-suc-PMO[$C^{bz}$-$C^{bz}$]-Tr (2.01 g, corresponding to 0.97 mmol) was ice-cooled, and a solution of trifluoroacetic acid (0.95 g, 8.36 mmol) in chloroform was added dropwise. Then, 2,2,2-trifluoroethanol (4.33 mL, 59.4 mmol) and thiomalic acid (1.45 g, 9.68 mmol) were added thereto. Furthermore, a chloroform solution (13.7 mL) of trifluoroacetic acid (0.88 g, 7.75 mmol) and triethylamine (0.48 g, 4.84 mmol) was added dropwise, and the mixture was stirred at 15° C. for 1.5 hours. A chloroform solution (30 mL) of N,N-diisopropylethylamine (3.00 g, 23.2 mmol) was added dropwise. The reaction mixture was washed successively with a mixed solution (4:1, 80 mL) of 5% aqueous sodium carbonate solution and N,N-dimethylformamide, a mixed solution (3:2, 80 mL) of 20% brine and N,N-dimethylformamide, and 20% brine (80 mL×2). The solvent was evaporated under reduced pressure, and the organic layer containing the obtained Bzl(3,4,5-OPhy)-O-suc-PMO[$C^{bz}$-$C^{bz}$]-H was directly subjected to the subsequent reaction.

TOF-MS+ (m/z) 915.1 (M+2H)$^+$

According to the methods of the above-mentioned 3) and 4), condensation and deprotection of trityl group were successively performed in one-pot without isolation of the objective compound to achieve elongation to 7 mer.

5) Deprotection of Trityl Group-7

The organic layer containing Bzl(3,4,5-OPhy)-O-suc-PMO[$C^{bz}$-$C^{bz}$-T-$C^{bz}$-$C^{bz}$-$G^{ce/pac}$-$G^{ce/pac}$]-Tr (4.19 g, corresponding to 0.97 mmol) was washed with 5 vol % 2,2,2-trifluoroethanolaqueous solution (50 mL×2) and, after ice-cooling the organic layer, 2,2,2-trifluoroethanol (9.8 mL, 135 mmol) and thiomalic acid (0.44 g, 2.90 mmol) were added thereto. Then, a chloroform solution (13.7 mL) of trifluoroacetic acid (0.88 g, 7.75 mmol) and triethylamine (0.48 g, 4.84 mmol) was added dropwise, and the mixture was stirred at 15° C. for 1 hour. Furthermore, a chloroform solution (12.5 mL) of N,N-diisopropylethylamine (1.25 g, 9.68 mmol) was added dropwise. The reaction mixture was washed successively with a mixed solution (4:1, 70 mL) of 5% aqueous sodium carbonate solution and N,N-dimethylformamide, a mixed solution (3:2, 70 mL×2) of 20% brine and N,N-dimethylformamide, and 20% brine (80 mL). The solvent was evaporated under reduced pressure, and the organic layer containing the obtained Bzl(3,4,5-OPhy)-O-suc-PMO[$C^{bz}$-$C^{bz}$-T-$C^{bz}$-$C^{bz}$-$G^{ce/pac}$-$G^{ce/pac}$]-H was directly subjected to the subsequent reaction.

TOF-MS+ (m/z) 1361.2 (M+3H)$^+$

6) Condensation-8

N,N-diisopropylethylamine (0.30 mL, 1.74 mmol) and Cl-mo-(Tr)T (0.89 g, 1.45 mmol) were added to the organic layer containing Bzl(3,4,5-OPhy)-O-suc-PMO[$C^{bz}$-$C^{bz}$-T-$C^{bz}$-$C^{bz}$-$G^{ce/pac}$-$G^{ce/pac}$]-H (3.95 g, corresponding to 0.97 mmol), and the mixture was stirred at room temperature for 15 hours. The reaction mixture was ice-cooled, N,N-diisopropylethylamine (2.08 mL, 12.1 mmol), prolylglutamic acid (0.59 g, 2.42 mmol) and 2,2,2-trifluoroethanol (10 mL, 137 mmol) were added thereto, and the mixture was stirred at room temperature for 4 hr. The obtained solution was washed with water (70 mL×2), and the organic layer containing Bzl(3,4,5-OPhy)-O-suc-PMO[$C^{bz}$-$C^{bz}$-T-$C^{bz}$-$C^{bz}$-$G^{ce/pac}$-$G^{ce/pac}$-T]-Tr was directly subjected to the subsequent reaction.

TOF-MS+ (m/z) 1552.0 (M+3H)$^+$

7) Deprotection of Trityl Group-8

The organic layer containing Bzl(3,4,5-OPhy)-O-suc-PMO[$C^{bz}$-$C^{bz}$-T-$C^{bz}$-$C^{bz}$-$G^{ce/pac}$-$G^{ce/pac}$-T]-Tr (4.51 g, corresponding to 0.97 mmol) was washed with 5 vol % aqueous 2,2,2-trifluoroethanol (50 mL×2), the organic layer was ice-cooled, and 2,2,2-trifluoroethanol (10 mL, 135 mmol) and thiomalic acid (0.44 g, 2.90 mmol) were added thereto. Then, a chloroform solution (13.7 mL) of trifluoroacetic acid (0.88 g, 7.75 mmol) and triethylamine (0.48 g, 4.84 mmol) was added dropwise, and the mixture was stirred at 15° C. for 1 hour. Furthermore, a chloroform solution (12.5 mL) of N,N-diisopropylethylamine (1.25 g, 9.68 mmol) was added dropwise. The reaction mixture was washed successively with a mixed solution (4:1, 90 mL) of 5% aqueous sodium carbonate and N,N-dimethylformamide, a mixed solution (3:2, 90 mL×2) of 20% brine and N,N-dimethylformamide, and 20% brine (90 mL). The solvent was concentrated under reduced pressure, and the organic layer containing the obtained Bzl(3,4,5-OPhy)-O-suc-PMO[$C^{bz}$-$C^{bz}$-T-$C^{bz}$-$C^{bz}$-$G^{ce/pac}$-$G^{ce/pac}$-T]-H was directly subjected to the subsequent reaction.

TOF-MS+ (m/z) 1471.3 (M+3H)$^+$

8) Condensation-9

N,N-diisopropylethylamine (0.30 mL, 1.74 mmol) and Cl-mo-(Tr)T (0.89 g, 1.45 mmol) were added to the organic layer containing Bzl(3,4,5-OPhy)-O-suc-PMO[$C^{bz}$-$C^{bz}$-T-$C^{bz}$-$C^{bz}$-$G^{ce/pac}$-$G^{ce/pac}$-T]-H (4.27 g, corresponding to 0.97 mmol), and the mixture was stirred at room temperature for 15 hours. The reaction mixture was ice-cooled, N,N-diisopropylethylamine (2.08 mL, 12.1 mmol), prolylglutamic acid (0.59 g, 2.42 mmol) and 2,2,2-trifluoroethanol (10 mL, 137 mmol) were added thereto, and the mixture was stirred at room temperature for 2 hours. A solution of trifluoroacetic acid (1.60 g, 14.0 mmol) in chloroform was added dropwise to the obtained solution, and the mixture was washed with water (70 mL×3). The organic layer was concentrated, acetonitrile (30 mL) was added to the obtained residue under ice-cooling, and the precipitate was collected by filtration and dried under reduced pressure to give Bzl(3,4,5-OPhy)-O-suc-PMO[$C^{bz}$-$C^{bz}$-T-$C^{bz}$-$C^{bz}$-$G^{ce/pac}$-$G^{ce/pac}$-T-T]-Tr (3.57 g, 0.72 mmol, yield 72% vs Bzl(3,4,5-OPhy)-OH) as a pale-yellow powder.

TOF-MS+ (m/z) 1662.0 (M+3H)$^+$

9) Mass Spectrometry after Deprotection

Ethanol (0.05 mL) and 28% aqueous ammonia (0.15 mL) were added to Bzl(3,4,5-OPhy)-O-suc-PMO[$C^{bz}$-$C^{bz}$-T-$C^{bz}$-$C^{bz}$-$G^{ce/pac}$-$G^{ce/pac}$-T-T]-Tr (5 mg), and the mixture was stirred at 55° C. for 15 hours. Acetonitrile (0.1 mL) and cyclohexane (0.3 mL) were added to the reaction mixture, and the aqueous layer was washed with cyclohexane (0.3 mL×2). A 50% aqueous methanol solution (0.7 mL) was added to the aqueous layer and the resulting solid was removed by filtration. Mass spectrometry of the aqueous solution of the obtained PMO[C-C-T-C-C-G-G-T-T]-Tr was performed.

TOF-MS+ (m/z) 1039.0 (M+3H)$^+$

1') Another Method of Condensation-1

Bzl(3,4,5-OPhy)-OH (3.0 g, 3.01 mmol) was dissolved in chloroform (30 mL), suc-mo(Tr)$C^{bz}$ (2.43 g, 3.61 mmol), 1-(3-dimethylaminopropyl)-3-ethylcarbodiimide hydrochloride (0.69 g, 3.61 mmol) and 4-dimethylaminopyridine (22 mg, 0.18 mmol) were added, and the mixture was stirred at room temperature for 17 hours. The solvent was evaporated under reduced pressure, and the residue was dissolved in cyclohexane (30 mL) and heptane (30 mL). Acetonitrile (30 mL) was added thereto and the m mixture was partition-washed twice. The solvent in the upper layer was evaporated under reduced pressure, and the mixture was dried under reduced pressure to give Bzl(3,4,5-OPhy)-O-suc-mo(Tr)$C^{bz}$ (4.67 g, 99%) as an oil.

TOF-MS+ (m/z) 1652.0

2') Another Method of Deprotection of Trityl Group-1

Bzl(3,4,5-OPhy)-O-suc-mo(Tr)$C^{bz}$ (0.30 g, 0.18 mmol) was dissolved in chloroform (3 mL), and 2,2,2-trifluoroethanol (0.79 mL, 10.9 mmol) and 3-mercaptopropionic acid (0.08 mL, 0.91 mmol) were added thereto. The mixture was ice-cooled, a solution of trifluoroacetic acid (0.16 g, 1.45 mmol) and triethylamine (0.10 g, 0.91 mmol) in chloroform was added dropwise, and the mixture was stirred at room temperature for 1.5 hours. The reaction mixture was ice-cooled, and a solution of N,N-diisopropylethylamine (0.19 g, 1.45 mmol) in chloroform was added dropwise. The obtained solution was washed successively with a mixed solution (3:2, 3 mL×2) of 10% aqueous sodium carbonate solution and N,N-dimethylformamide, 40% aqueous N,N-dimethylformamide solution (5 mL) and 20% brine (3 mL) to give an organic layer containing Bzl(3,4,5-OPhy)-O-suc-mo$C^{bz}$, and the organic layer was directly subjected to the subsequent reaction.

2") Another Method of Deprotection of Trityl Group-1

Bzl(3,4,5-OPhy)-O-suc-mo(Tr)$C^{bz}$ (0.80 g, 0.48 mmol) was dissolved in chloroform (6.4 mL), and 2,2,2-trifluoroethanol (2.1 mL, 29.0 mmol) and thiomalic acid (0.22 g, 1.45 mmol) were added thereto. After ice-cooling, a chloroform solution (1.5 mL) of trifluoroacetic acid (0.44 g, 3.87 mmol) and triethylamine (0.24 g, 2.42 mmol) was added dropwise to the mixture, and the mixture was stirred at 15° C. for 90 minutes. The reaction mixture was ice-cooled, and a chloroform solution (1.7 mL) of N,N-diisopropylethylamine (0.25 g, 1.94 mmol) was added dropwise. The obtained solution was washed successively with a mixed solution (4:1, 8 mL×2) of 5% aqueous sodium carbonate and N,N-dimethylformamide and a mixed solution (3:2, 8 mL×3) of 20% brine and N,N-dimethylformamide to give an organic layer containing Bzl(3,4,5-OPhy)-O-suc-mo$C^{bz}$, and the organic layer was directly subjected to the subsequent reaction.

TOF-MS+ (m/z) 1410.1

3') Another Method of Condensation-2

To the organic layer containing Bzl(3,4,5-OPhy)-O-suc-mo$C^{bz}$ (0.25 g, corresponding to 0.18 mmol) were added N,N-diisopropylethylamine (0.06 mL, 0.33 mmol) and Cl-mo-(Tr)$C^{bz}$ (0.19 g, 0.27 mmol), and the mixture was stirred at room temperature for 17 hours. To the reaction mixture were added N,N-diisopropylethylamine (0.01 mL, 0.04 mmol) and Cl-mo-(Tr)$C^{bz}$ (0.03 g, 0.04 mmol), and the mixture was stirred at room temperature for 2 hours. Furthermore, morpholine (0.022 mL, 0.25 mmol) was added to the reaction mixture. The obtained organic layer containing Bzl(3,4,5-OPhy)-O-suc-PMO[$C^{bz}$-$C^{bz}$]-Tr was directly subjected to the subsequent reaction.

3") Another Method of Condensation-2

To the organic layer containing Bzl(3,4,5-OPhy)-O-suc-moC$^{bz}$ (corresponding to 0.24 mmol) were added N,N-diisopropylethylamine (0.07 mL, 0.38 mmol) and Cl-mo-(Tr)C$^{bz}$ (0.22 g, 0.32 mmol), and the mixture was stirred at room temperature for 52 hours. After the reaction, N,N-diisopropylethylamine (0.32 mL, 1.82 mmol), prolylglutamic acid (0.09 g, 0.36 mmol) and 2,2,2-trifluoroethanol (0.94 mL) were added, and the mixture was stirred at room temperature for 3 hours. The mixture was washed with a mixed solution (1:19, 3.5 mL×2) of 2,2,2-trifluoroethanol and 0.1 mM hydrochloric acid to give an organic layer containing Bzl(3,4,5-OPhy)-O-suc-PMO[C$^{bz}$-C$^{bz}$]-Tr, and the organic layer was directly subjected to the subsequent reaction.

TOF-MS+ (m/z) 2071.8

Example 2: Change of Quenching Agent in Example 1, 3) (Quenching Agent: L-Prolyl L-Proline)

Bzl(3,4,5-OPhy)-O-suc-mo(Tr)C$^{bz}$ (0.80 g, 0.48 mmol) was dissolved in chloroform (6.4 mL), and 2,2,2-trifluoroethanol (2.1 mL, 29.0 mmol) and thiomalic acid (0.22 g, 1.45 mmol) were added thereto. The mixture was ice-cooled, a chloroform solution (1.5 mL) of trifluoroacetic acid (0.44 g, 3.87 mmol) and triethylamine (0.24 g, 2.42 mmol) was added dropwise, and the mixture was stirred at 15° C. for 90 minutes. The reaction mixture was ice-cooled, and a chloroform solution (1.7 mL) of N,N-diisopropylethylamine (0.25 g, 1.94 mmol) was added dropwise. The obtained solution was washed successively with a mixed solution (4:1, 8 mL×2) of 5% aqueous sodium carbonate and N,N-dimethylformamide and a mixed solution (3:2, 8 mL×3) of 20% brine and N,N-dimethylformamide to give an organic layer containing Bzl(3,4,5-OPhy)-O-suc-moC$^{bz}$, and the organic layer was directly subjected to the subsequent reaction.

TOF-MS+ (m/z) 1410.1

To the organic layer containing Bzl(3,4,5-OPhy)-O-suc-moC$^{bz}$ (corresponding to 0.24 mmol) were added N,N-diisopropylethylamine (0.07 mL, 0.38 mmol) and Cl-mo-(Tr)C$^{Bz}$ (0.22 g, 0.32 mmol), and the mixture was stirred at room temperature for 52 hours. N,N-diisopropylethylamine (0.32 mL, 1.82 mmol), L-prolyl L-proline (0.07 g, 0.36 mmol) and 2,2,2-trifluoroethanol (0.94 mL) were added to the reaction mixture, and the mixture was stirred at room temperature for 3 hours. The reaction mixture was washed with a mixed solution (1:19, 3.5 mL×2) of 2,2,2-trifluoroethanol and 0.1 mM hydrochloric acid to give an organic layer containing Bzl(3,4,5-OPhy)-O-suc-PMO[C$^{bz}$-C$^{bz}$]-Tr.

TOF-MS+ (m/z) 2071.8

Example 3: Change of Cation Scavenger in Example 1, 2) (Cation Scavenger: 1-(1H-Indol-5-Yl) Butanedicarboxylate)

Bzl(3,4,5-OPhy)-O-suc-mo (Tr)C$^{bz}$ (0.80 g, 0.48 mmol) was dissolved in chloroform (6.4 mL), and 2,2,2-trifluoroethanol (2.1 mL, 29.0 mmol) and 1-(1H-indol-5-yl) butanedicarboxylate (0.34 g, 1.45 mmol) were added thereto. The mixture was ice-cooled, a chloroform solution (1.5 mL) of trifluoroacetic acid (0.44 g, 3.87 mmol) and triethylamine (0.24 g, 2.42 mmol) was added dropwise, and the mixture was stirred at 15° C. for 90 minutes. The reaction mixture was ice-cooled, and a chloroform solution (1.7 mL) of N,N-diisopropylethylamine (0.25 g, 1.94 mmol) was added dropwise. The obtained solution was washed successively with a mixed solution (4:1, 8 mL×2) of 5% aqueous sodium carbonate and N,N-dimethylformamide and a mixed solution (3:2, 8 mL×3) of 20% brine and N,N-dimethylformamide to give an organic layer containing Bzl(3,4,5-OPhy)-O-suc-moC$^{bz}$, and the organic layer was directly subjected to the subsequent reaction.

TOF-MS+ (m/z) 1410.1

To the organic layer containing Bzl(3,4,5-OPhy)-O-suc-moC$^{bz}$ (corresponding to 0.24 mmol) were added N,N-diisopropylethylamine (0.07 mL, 0.38 mmol) and Cl-mo-(Tr)C$^{bz}$ (0.22 g, 0.32 mmol), and the mixture was stirred at room temperature for 52 hours. N,N-diisopropylethylamine (0.32 mL, 1.82 mmol), L-prolyl L-glutamic acid (0.09 g, 0.36 mmol) and 2,2,2-trifluoroethanol (0.94 mL) were added to the reaction mixture, and the mixture was stirred at room temperature for 3 hours. The reaction mixture was washed with a mixed solution (1:19, 3.5 mL×2) of 2,2,2-trifluoroethanol and 0.1 mM hydrochloric acid to give an organic layer containing Bzl(3,4,5-OPhy)-O-suc-PMO[C$^{bz}$-C$^{bz}$]-Tr.

TOF-MS+ (m/z) 2071.8

Example 4: Change of Quenching Agent in Example 1, 3) (Quenching Agent: Phenylphosphonic Acid)

Bzl(3,4,5-OPhy)-O-suc-mo(Tr)C$^{bz}$ (1.0 g, 0.61 mmol) was dissolved in chloroform (8.0 mL), and 2,2,2-trifluoroethanol (2.6 mL, 36.3 mmol) and thiomalic acid (0.27 g, 1.82 mmol) were added thereto. The mixture was ice-cooled, a chloroform solution (1.9 mL) of trifluoroacetic acid (0.55 g, 4.84 mmol) and triethylamine (0.31 g, 3.03 mmol) was added dropwise, and the mixture was stirred at 15° C. for 120 minutes. The reaction mixture was ice-cooled, and a chloroform solution (2.1 mL) of N,N-diisopropylethylamine (0.31 g, 2.42 mmol) was added dropwise. The obtained solution was washed successively with a mixed solution (4:1, 10 mL×2) of 5% aqueous sodium carbonate and N,N-dimethylformamide and a mixed solution (3:2, 10 mL×3) of 20% brine and N,N-dimethylformamide to give an organic layer containing Bzl(3,4,5-OPhy)-O-suc-moC$^b$z, and the organic layer was directly subjected to the subsequent reaction.

TOF-MS+ (m/z) 1410.1

To the organic layer containing Bzl(3,4,5-OPhy)-O-suc-moC$^{bz}$ (corresponding to 0.61 mmol) were added N,N-diisopropylethylamine (0.16 mL, 0.94 mmol) and Cl-mo-(Tr)C$^{bz}$ (0.55 g, 0.79 mmol), and the mixture was stirred at room temperature for 16 hours. N,N-diisopropylethylamine (0.79 mL, 4.54 mmol), phenylphosphonic acid (0.14 g, 0.91 mmol) and 2,2,2-trifluoroethanol (2.33 mL) were added to the reaction mixture, and the mixture was stirred at room temperature for 2 hr, phenylphosphonic acid (0.57 g, 3.63 mmol) and N,N-diisopropylethylamine (0.78 mL, 4.50 mmol) were further added thereto, and the mixture was stirred at room temperature for 1 hour. The reaction mixture was washed with a mixed solution (1:19, 8.5 mL×2) of 2,2,2-trifluoroethanol and 0.1 mM hydrochloric acid to give an organic layer containing Bzl(3,4,5-OPhy)-O-suc-PMO [$C^{bz}$-$C^{bz}$]-Tr.

TOF-MS+ (m/z) 2071.8

Example 5: Elongation Reaction of Substrate Having Dpm(4,4'-OPhy)-NH-Containing Anchor on the 5'-Terminus (1.9 mL, 26.1 mmol) and thiomalic acid (0.58 g, 3.85 mmol) were added thereto. The mixture was ice-cooled, a chloroform solution (5.5 mL) of trifluoroacetic acid (0.35 g, 3.08 mmol) and triethylamine (0.19 g, 1.93 mmol) was added dropwise, and the mixture was stirred at 15° C. for 1.5 hours. The reaction mixture was ice-cooled, and a chloroform solution (12 mL) of N,N-diisopropylethylamine (1.20 g, 9.25 mmol) was added dropwise. The obtained solution was

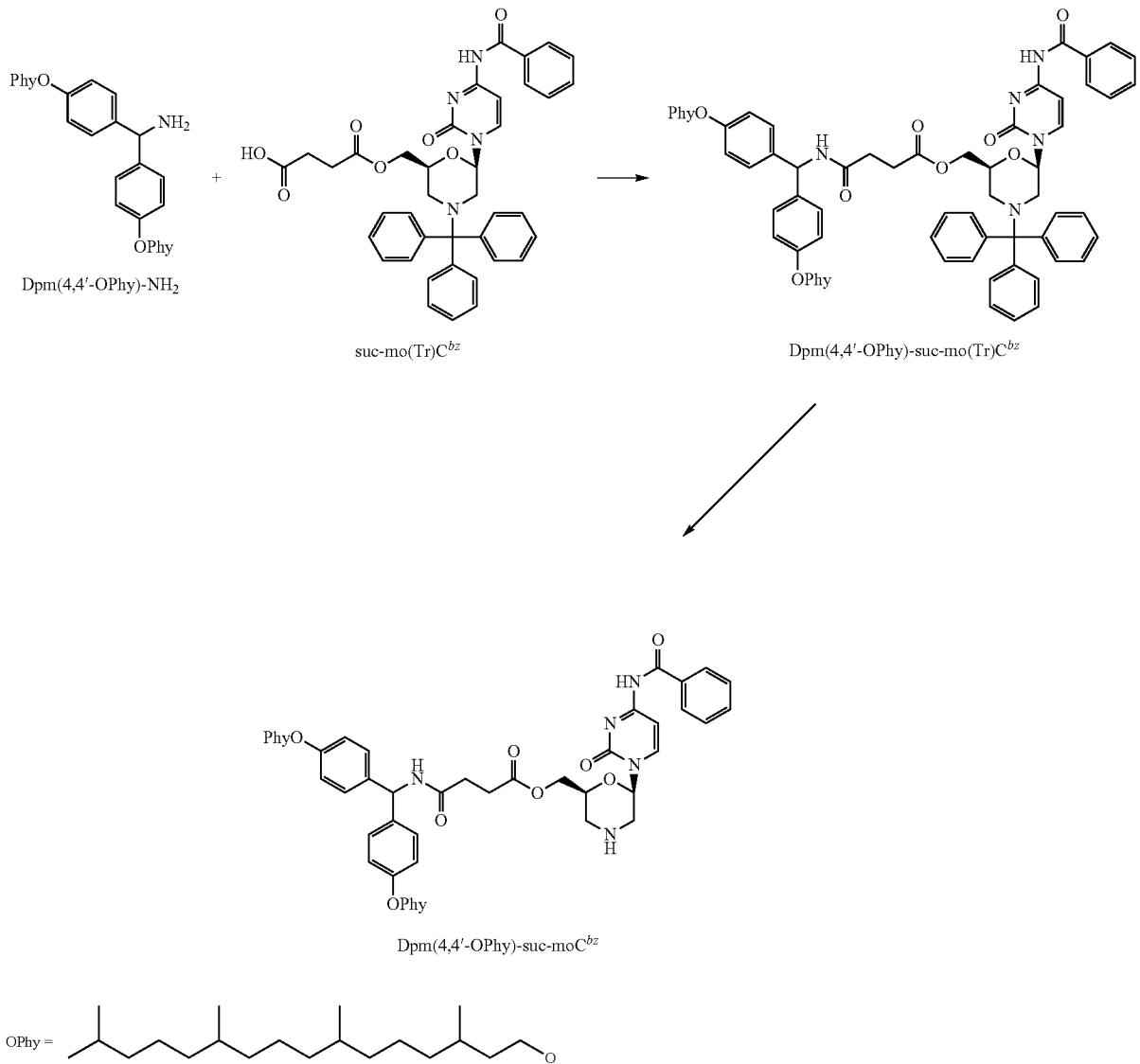

1) Condensation-1

Dpm(4,4'-OPhy)-NH$_2$ (0.30 g, 0.39 mmol) was dissolved in chloroform (3 mL), suc-mo(Tr)$C^{bz}$ (0.10 g, 0.15 mmol) and 1-(3-dimethylaminopropyl)-3-ethylcarbodiimide hydrochloride (0.04 g, 0.17 mmol) were added thereto, and the mixture was stirred at room temperature for 21 hours. Chloroform (10 mL) was added to the reaction mixture, and the mixture was washed with 20% brine (10 mL), and a solution containing the obtained Dpm(4,4'-OPhy)-suc-mo(Tr)$C^{bz}$ was directly subjected to the subsequent reaction.

TOF-MS+ (m/z) 1430.8

2) Deprotection of Trityl Group-1

Dpm(4,4'-OPhy)-suc-mo(Tr)$C^{bz}$ (0.55 g, 0.39 mmol) was dissolved in chloroform (6 mL), and 2,2,2-trifluoroethanol washed successively with a mixed solution (4:1, 25 mL) of 5% aqueous sodium carbonate and N,N-dimethylformamide, a mixed solution (3:2, 25 mL×2) of 20% brine and N,N-dimethylformamide, and 20% brine (25 mL×2), and the organic layer was concentrated under reduced pressure to give Dpm(4,4'-OPhy)-suc-mo$C^{bz}$.

TOF-MS+ (m/z) 1188.8

Example 6: Elongation Reaction of Substrate Having cHxCH$_2$(3,4,5-OPhy)-O-Containing Anchor on the 5'-Terminus

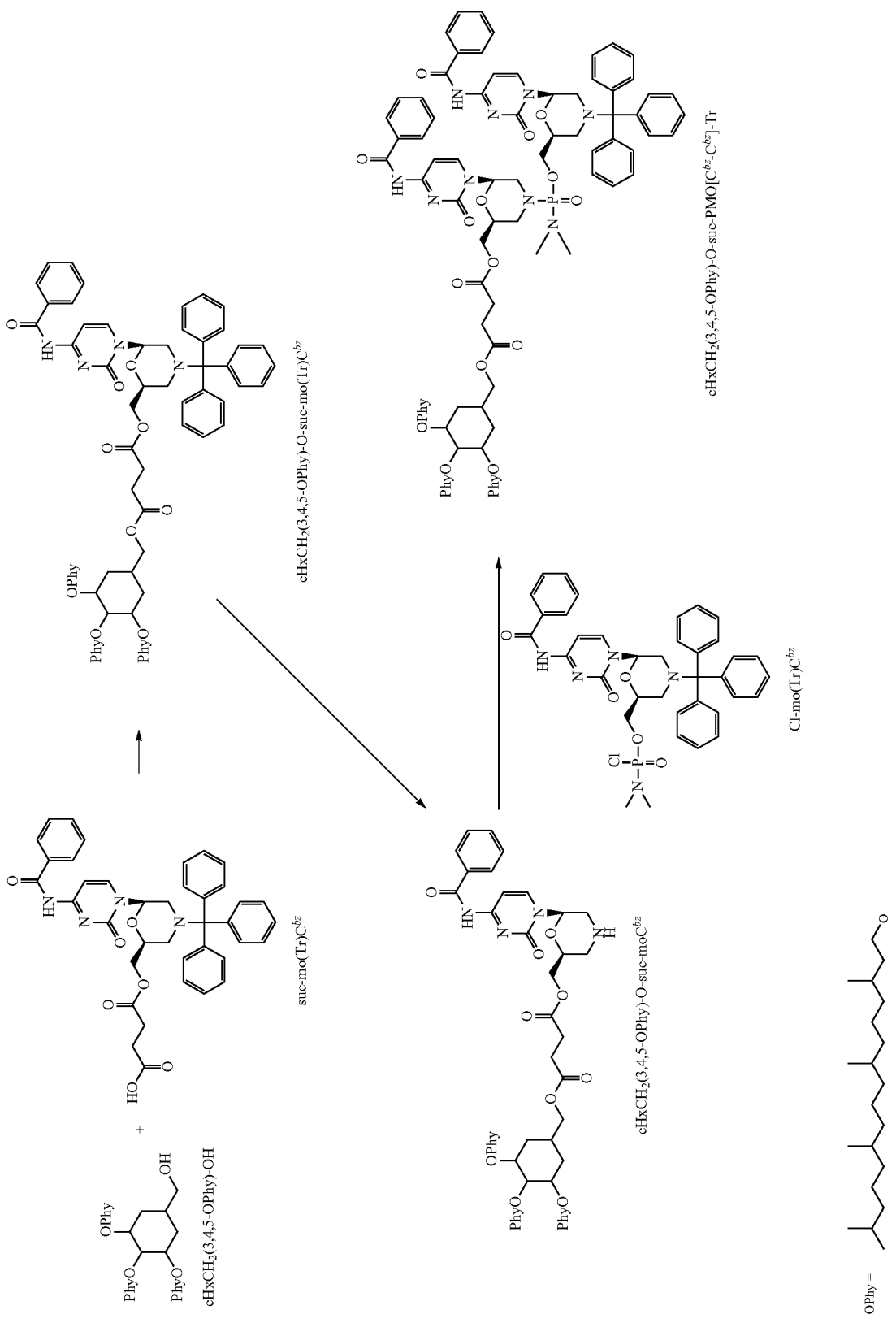

1) Condensation-1 cHxCH$_2$(3,4,5-OPhy)-OH (1.0 g, 1.09 mmol) was dissolved in chloroform (10 mL), suc-mo(Tr)C$^{bz}$ (0.95 g, 1.41 mmol), 1-(3-dimethylaminopropyl)-3-ethylcarbodiimide hydrochloride (0.27 g, 1.41 mmol) and 4-dimethylaminopyridine (9 mg, 0.07 mmol) were added thereto, and the mixture was stirred at room temperature for 23 hours. The solvent was evaporated under reduced pressure. The residue was dissolved in cyclohexane (30 mL) and heptane (30 mL), and the mixture was partition-washed twice with acetonitrile (30 mL). The solvent in the upper layer was evaporated under reduced pressure, and methanol (10 mL) was added to the residue and the solid was slurry-washed to give cHxCH$_2$(3,4,5-OPhy)-O-suc-mo(Tr)C$^{bz}$ (1.62 g, 100%) as a colorless solid.

TOF-MS+ (m/z) 1574.8

2) Deprotection of Trityl Group-1 cHxCH$_2$ (3,4,5-OPhy)-O-suc-mo(Tr)C$^{bz}$ (1.00 g, 0.64 mmol) was dissolved in chloroform (8.0 mL), and 2,2,2-trifluoroethanol (2.7 mL, 38.1 mmol) and thiomalic acid (0.29 g, 1.90 mmol) were added thereto. After ice-cooling, a chloroform solution (1.9 mL) of trifluoroacetic acid (0.58 g, 5.08 mmol) and triethylamine (0.32 g, 3.17 mmol) was added dropwise to the mixture, and the mixture was stirred at 15° C. for 150 minutes. The reaction mixture was ice-cooled, and a chloroform solution (2.2 mL) of N,N-diisopropylethylamine (0.33 g, 2.54 mmol) was added dropwise. The obtained solution was washed successively with a mixed solution (4:1, 10 mL×2) of 5% aqueous sodium carbonate and N,N-dimethylformamide and a mixed solution (3:2, 10 mL×3) of 20% brine and N,N-dimethylformamide to give an organic layer containing cHxCH$_2$(3,4,5-OPhy)-O-suc-moC$^{bz}$, and the organic layer was directly subjected to the subsequent reaction.

TOF-MS+ (m/z) 1331.7

3) Condensation-2

To the organic layer containing cHxCH$_2$(3,4,5-OPhy)-O-suc-moC$^{bz}$ (corresponding to 0.64 mmol) were added N,N-diisopropylethylamine (0.17 mL, 0.99 mmol) and Cl-mo-(Tr)C$^{bz}$ (0.58 g, 0.83 mmol), and the mixture was stirred at room temperature for 16 hours. To the reaction mixture were added N,N-diisopropylethylamine (0.83 mL, 4.76 mmol), prolylglutamic acid (0.23 g, 0.95 mmol) and 2,2,2-trifluoroethanol (2.36 mL), and the mixture was stirred at room temperature for 2 hr. The reaction mixture was washed with a mixed solution (1:19, 8.5 mL×2) of 2,2,2-trifluoroethanol and 0.1 mM hydrochloric acid to give an organic layer containing cHxCH$_2$(3,4,5-OPhy)-O-suc-PMO[C$^{bz}$-C$^{bz}$]-Tr.

TOF-MS+ (m/z) 1993.7

Example 7: Elongation Reaction Using Substrate without Containing Anchor

1) Introduction of Silyl Protecting Group 2-(N-benzoyl)cytosyl-6-hydroxymethyl-4-tritylmorpholine (4.00 g, 6.99 mmol) was dissolved in N,N-dimethylformamide (40 mL). The mixture was ice-cooled, imidazole (3.80 g, 55.9 mmol) and tert-butyldimethylsilyl chloride (4.21 g, 27.9 mmol) were added thereto, and the mixture was stirred at 40° C. for 2 hours. The reaction mixture was partition-washed with water (300 mL), ethyl acetate (150 mL) and hexane (150 mL). The upper layer was recovered and partition-washed with water (100 ml). The upper layer was recovered and the solvent was evaporated under reduced pressure, and the residue was dried under reduced pressure at 40° C. to give 2-(N-benzoyl)cytosyl-6-(tert-butyldimethylsiloxy)methyl-4-tritylmorpholine (5.80 g, 120%).

TOF-MS+ (m/z) 686.9

2) Deprotection of Trityl Group-1

2-(N-benzoyl)cytosyl-6-(tert-butyldimethylsiloxy)methyl-4-tritylmorpholine (0.10 g, 0.15 mmol) was dissolved in chloroform (0.50 mL), and 2,2,2-trifluoroethanol (0.15 mL, 2.09 mmol) and thiomalic acid (0.066 g, 0.44 mmol) were added thereto. The mixture was ice-cooled, a chloroform solution (0.35 mL) of trifluoroacetic acid (0.13 g, 1.17 mmol) and triethylamine (0.074 g, 0.73 mmol) was added dropwise, and the mixture was stirred at 15° C. for 2 hours. After ice-cooling, and a chloroform solution (0.51 mL) of N,N-diisopropylethylamine (0.75 g, 0.58 mmol) was added dropwise. The obtained solution was partition-washed with a mixed solution (4:1, 2.0 mL×2) of 5% aqueous sodium carbonate and N,N-dimethylformamide. The lower layer was recovered, and partition-washed with a mixed solution (3:2, 2.0 mL×3) of 20% brine and N,N-dimethylformamide and the lower layer was recovered. The organic layer containing 2-(N-benzoyl)cytosyl-6-(tert-butyldimethylsiloxy)methylmorpholine was concentrated under reduced pressure, and subjected to the subsequent reaction.

TOF-MS+ (m/z) 444.6

3) Condensation-2

To the organic layer (0.65 mL) containing 2-(N-benzoyl)cytosyl-6-(tert-butyldimethylsiloxy)methylmorpholine (0.065 g, corresponding to 0.15 mmol) were added N,N-diisopropylethylamine (0.046 mL, 0.26 mmol) and [2-(N-benzoyl)cytosyl-4-tritylmorpholin-6-yl]methyldimethylphosphoramide chloridate (0.15 g, 0.22 mmol), and the mixture was stirred at room temperature for 23 hours. To the reaction mixture were added N,N-diisopropylethylamine (0.32 mL, 1.82 mmol), prolylglutamic acid (0.089 g, 0.36 mmol) and 2,2,2-trifluoroethanol (0.14 mL, 1.93 mmol), and the mixture was stirred at room temperature for 3.5 hours. The mixture was partition-washed with water (2 mL×2), and a lower layer containing TBSO-PMO[C$^{bz}$-C$^{bz}$]-Trt was recovered, concentrated under reduced pressure and subjected to the subsequent reaction.

TOF-MS+ (m/z) 1106.3

4) Deprotection of Trityl Group-2

The organic layer (1.61 mL) containing TBSO-PMO[C$^{bz}$-C$^{bz}$]-Trt (0.16 g, corresponding to 0.15 mmol) was ice-cooled, and a solution of trifluoroacetic acid (0.23 g, 2.28 mmol) in chloroform (1.20 ml) was added dropwise. To the mixture were added 2,2,2-trifluoroethanol (0.67 mL, 8.79 mmol) and thiomalic acid (0.066 g, 0.44 mmol). Then, a chloroform solution (1.00 mL) of trifluoroacetic acid (0.13 g, 1.17 mmol) and triethylamine (0.044 g, 0.44 mmol) was added dropwise, the mixture was stirred at 15° C. for 1 hour, and a chloroform solution (0.50 mL) of N,N-diisopropylethylamine (0.075 g, 0.58 mmol) was added dropwise. The mixture was successively partition-washed with a mixed solution (4:1, 3.00 mL×2) of 5% aqueous sodium carbonate and N,N-dimethylformamide and a mixed solution (3:2, 3.00 mL×3) of 20% brine and N,N-dimethylformamide to recover a lower layer containing TBSO-PMO[C$^{bz}$-C$^{bz}$]-H, and the lower layer was concentrated under reduced pressure and subjected to the subsequent reaction.

TOF-MS+ (m/z) 864.0

5) Condensation-3

To the organic layer (1.26 mL) containing TBSO-PMO[C$^{bz}$-C$^{bz}$]-H (0.13 g, corresponding to 0.15 mmol) were added N,N-diisopropylethylamine (0.046 mL, 0.26 mmol) and (4-trityl-2-thymidylmorpholin-6-yl)methyldimethyl phosphoramide chloridate (0.13 g, 0.22 mmol), and the mixture was stirred at room temperature for 16 hours. To the reaction mixture were added N,N-diisopropylethylamine (0.32 mL, 1.82 mmol), prolylglutamic acid (0.089 g, 0.36 mmol) and 2,2,2-trifluoroethanol (0.67 mL, 9.41 mmol), and the mixture was stirred at room temperature for 2 hours. The mixture was partition-washed with water (2 mL×2), and a lower layer containing TBSO-PMO[$C^{bz}$-$C^{bz}$-T]-Trt was recovered, concentrated under reduced pressure and dried to give crystals containing the objective compound.

TOF-MS+ (m/z) 1436.6

Example 8: Elongation Reaction Using Substrate with Anchoring (Linear Anchor (Anchor Having Octadecyloxy Group) Protection) at Nucleic Acid Base Moiety Alone 1) Introduction of Silyl Protecting Group 2-Cytosyl-6-hydroxymethyl-4-tritylmorpholine (4.00 g, 8.54 mmol) was dissolved in N,N-dimethylformamide (40 mL). The mixture was ice-cooled, imidazole (4.65 g, 68.3 mmol) and tert-butyldimethylsilyl chloride (5.15 g, 34.1 mmol) were added thereto, and the mixture was heated to 40° C. and stirred for 2 hours. The reaction mixture was partition-washed with water (300 mL), ethyl acetate (150 mL) and hexane (150 mL). The upper layer was recovered and partition-washed with water (100 ml). The upper layer was recovered, concentrated under reduced pressure, and dried under reduced pressure at 40° C. to give 2-cytosyl-6-(tert-butyldimethylsiloxy)methyl-4-tritylmorpholine (6.23 g, 125%).

TOF-MS+ (m/z) 582.8

2) Anchoring of Nucleic Acid Base Moiety with Linear Anchor 3,4,5-Tri(octadecyloxy)benzoic acid (1.00 g, 1.08 mmol) was dissolved in chloroform (10 mL), and N,N-diisopropylethylamine (0.56 mL, 3.23 mmol) was added thereto. The mixture was ice-cooled, O-(benzotriazol-1-yl)-N,N,N',N'-tetramethyluronium hexafluorophosphate (0.61 g, 1.62 mmol) was added thereto, and the mixture was stirred at room temperature for 30 minutes. To the reaction mixture were added 2-cytosyl-6-(tert-butyldimethylsiloxy)methyl-4-tritylmorpholine (1.26 g, 2.16 mmol) and chloroform (1.0 mL), and the mixture was stirred at 40° C. for 16 hours. Acetonitrile (10 mL) was added to the reaction mixture and the mixture was concentrated under reduced pressure. Then, acetonitrile (10 mL) was added thereto and the mixture was stirred for 30 minutes to allow for crystallization. The obtained crystals were collected by filtration under reduced pressure, acetonitrile (10 mL) was added and the crystals were slurry washed. The obtained crystals were collected by filtration under reduced pressure and vacuum dried to give 2-[N-{3,4,5-tri(octadecyloxy)benzoyl}]cytosyl-6-(tert-butyldimethylsiloxy)methyl-4-tritylmorpholine (1.59 g, 99%).

TOF-MS+ (m/z) 1492.4

3) Deprotection of Trityl Group-1

2-[N-{3,4,5-tri(octadecyloxy)benzoyl}]cytosyl-6-(tert-butyldimethylsiloxy)methyl-4-tritylmorpholine (0.50 g, 0.34 mmol) was dissolved in chloroform (3.25 mL), and 2,2,2-trifluoroethanol (0.75 mL, 10.46 mmol) and thiomalic acid (0.15 g, 1.01 mmol) were added to the mixture. The mixture was ice-cooled, a chloroform solution (1.00 mL) of trifluoroacetic acid (0.31 g, 2.68 mmol) and triethylamine (0.17 g, 1.68 mmol) was added dropwise, and the mixture was stirred at 15° C. for 1.5 hours. The reaction mixture was ice-cooled, and a chloroform solution (1.20 mL) of N,N-diisopropylethylamine (0.17 g, 1.34 mmol) was added dropwise. The obtained solution was partition-washed with a mixed solution (4:1, 10.0 mL×2) of 5% aqueous sodium carbonate and N,N-dimethylformamide. The lower layer was recovered and partition-washed with a mixed solution (3:2, 10.0 mL×3) of 20% brine and N,N-dimethylformamide, and the lower layer was recovered. The organic layer containing 2-[N-(3,4,5-tri(octadecyloxy)benzoyl)]cytosyl-6-(tert-butyldimethylsiloxy)methylmorpholine was concentrated under reduced pressure, and subjected to the subsequent reaction.

TOF-MS+ (m/z) 1250.0

4) Condensation-2

To the organic layer (4.20 mL) containing 2-[N-{3,4,5-tri(octadecyloxy)benzoyl}]cytosyl-6-(tert-butyldimethylsiloxy)methylmorpholine (0.42 g, corresponding to 0.34 mmol) were added N,N-diisopropylethylamine (0.11 mL, 0.60 mmol) and {2-(N-benzoyl)cytosyl-4-tritylmorpholin-6-yl}methyldimethyl phosphoramide chloridate (0.35 g, 0.50 mmol), and the mixture was stirred at room temperature for 19.5 hours. To the reaction mixture were added N,N-diisopropylethylamine (0.73 mL, 4.19 mmol), prolylglutamic acid (0.20 g, 0.84 mmol) and 2,2,2-trifluoroethanol (0.90 mL, 12.5 mmol), and the mixture was stirred at room temperature for 1 hour. The mixture was partition-washed with water (6.30 mL×2), and the lower layer containing TBSO-PMO[$C^{TOB}$-$C^{bz}$]-Trt was recovered, concentrated under reduced pressure, and subjected to the subsequent reaction.

TOF-MS+ (m/z) 1911.7

5) Deprotection of Trityl Group-2

The organic layer (7.50 mL) containing TBSO-PMO [$C^{TOB}$-$C^{bz}$]-Trt (0.75 g, corresponding to 0.34 mmol) was ice-cooled, and a solution of trifluoroacetic acid (0.35 g, 3.43 mmol) in chloroform (3.47 ml) was added dropwise. To the mixture were added 2,2,2-trifluoroethanol (2.11 mL, 27.6 mmol) and thiomalic acid (0.15 g, 1.01 mmol). Then, a chloroform solution (1.00 mL) of trifluoroacetic acid (0.31 g, 2.68 mmol) and triethylamine (0.17 g, 1.68 mmol) was added dropwise, and the mixture was stirred at 15° C. for 1.5 hours. A chloroform solution (0.50 mL) of N,N-diisopropylethylamine (0.17 g, 1.34 mmol) was added dropwise. The mixture was successively partition-washed with a mixed solution (4:1, 7.50 mL×2) of 5% aqueous sodium carbonate and N,N-dimethylformamide and a mixed solution (3:2, 7.50 mL×3) of 20% brine and N,N-dimethylformamide. The lower layer containing TBSO-PMO[$C^{TOB}$-$C^{bz}$]-H was recovered, concentrated under reduced pressure and subjected to the subsequent reaction.

TOF-MS+ (m/z) 1669.4

6) Condensation-3

To the organic layer (5.60 mL) containing TBSO-PMO [$C^{TOB}$-$C^{bz}$]-H (0.56 g, corresponding to 0.34 mmol) were added N,N-diisopropylethylamine (0.11 mL, 0.60 mmol) and (4-trityl-2-thymidylmorpholin-6-yl)methyldimethyl phosphoramide chloridate (0.31 g, 0.50 mmol), and the mixture was stirred at room temperature for 18 hours. To the reaction mixture were added N,N-diisopropylethylamine (0.73 mL, 4.19 mmol), prolylglutamic acid (0.20 g, 0.84 mmol) and 2,2,2-trifluoroethanol (2.71 mL, 37.8 mmol), and the mixture was stirred at room temperature for 1 hour. The mixture was partition-washed with water (11.2 mL×2), and the lower layer containing TBSO-PMO[$C^{TOB}$-$C^{bz}$-T]-Trt was recovered, and concentrated under reduced pressure. Acetonitrile (22.4 mL) was added thereto to allow for precipitation and the precipitate was collected by filtration under reduced pressure. Acetonitrile (11.2 mL) was added to the obtained crystals and the mixture was slurry washed. The crystals were collected by filtration under reduced pressure and vacuum dried to give the objective compound (0.63 g, 84%).

TOF-MS+ (m/z) 2242.0

Example 9: Elongation Reaction Using Substrate with Anchoring (Branched Chain Anchor (Anchor Having 2',3'-Dihydrophytyloxy Group) Protection) at Nucleic Acid Base Moiety Alone 1) Anchoring of Nucleic Acid Base Moiety with Branched Chain Anchor 3,4,5-Tri(2',3'-dihydrophytyloxy)benzoic acid (2.00 g, 1.98 mmol) was dissolved in chloroform (16 mL), and N,N-diisopropylethylamine (0.77 mL, 5.93 mmol) was added thereto. The mixture was ice-cooled, O-(benzotriazol-1-yl)-N,N,N',N'-tetramethyluronium hexafluorophosphate (1.12 g, 2.97 mmol) was added thereto, and the mixture was stirred at room temperature for 30 minutes. To the reaction mixture were added 2-cytosyl-6-(tert-butyldimethylsiloxy) methyl-4-tritylmorpholine (2.30 g, 3.95 mmol) and chloroform (4.0 mL), and the mixture was stirred at 40° C. for 17 hours. The reaction mixture was partition-washed with saturated aqueous sodium hydrogen carbonate solution (60 mL) and chloroform (40 mL), and the recovered lower layer was partition-washed with 20% brine (60 mL×2). The obtained lower layer was concentrated under reduced pressure, and partition-washed with cyclohexane (60 mL), heptane (20 mL) and acetonitrile (60 mL). The recovered lower layer was partition-washed with cyclohexane (30 mL) and heptane (15 mL). The upper layers obtained by twice of partition-washing were mixed, and the mixture was partition-washed with acetonitrile (30 mL). The upper layer was recovered, concentrated under reduced pressure, and dried under reduced pressure at 40° C. to give 2-[N-{3,4,5-tri(2',3'-dihydrophytyloxy)benzoylamino}]cytosyl-6-(tert-butyldimethylsiloxy)methyl-4-tritylmorpholine (3.47 g, 112%).

TOF-MS+ (m/z) 1576.5

2) Deprotection of Trityl Group-1

2-[N-{3,4,5-tri(2',3'-dihydrophytyloxy)benzoylamino}]cytosyl-6-(tert-butyldimethylsiloxy)methyl-4-tritylmorpholine (1.00 g, 0.63 mmol) was dissolved in chloroform (6.50 mL), and 2,2,2-trifluoroethanol (1.50 mL, 20.9 mmol) and thiomalic acid (0.29 g, 1.90 mmol) were added to the mixture. The mixture was ice-cooled, a chloroform solution (2.0 mL) of trifluoroacetic acid (0.58 g, 5.07 mmol) and triethylamine (0.32 g, 3.17 mmol) was added dropwise, and the mixture was stirred at 15° C. for 1 hour. The reaction mixture was ice-cooled, and a chloroform solution (2.2 mL) of N,N-diisopropylethylamine (0.33 g, 2.54 mmol) was added dropwise. The obtained solution was partition-washed with a mixed solution (4:1, 20 mL×2) of 5% aqueous sodium carbonate and N,N-dimethylformamide. The lower layer was recovered, and partition-washed with a mixed solution (3:2, 20 mL×3) of 20% brine and N,N-dimethylformamide, and the lower layer was recovered. The organic layer containing 2-[N-{3,4,5-tri(2',3'-dihydrophytyloxy)benzoylamino}]cytosyl-6-(tert-butyldimethylsiloxy)methylmorpholine was concentrated under reduced pressure, and subjected to the subsequent reaction.

TOF-MS+ (m/z) 1334.2

3) Condensation-2

To the organic layer (8.50 mL) containing 2-[N-{3,4,5-tri(2',3'-dihydrophytyloxy)benzoylamino}]cytosyl-6-(tert-butyldimethylsiloxy)methylmorpholine (0.85 g, corresponding to 0.63 mmol) were added N,N-diisopropylethylamine (0.20 mL, 1.14 mmol) and (4-trityl-2-thymidylmorpholin-6-yl)methyldimethyl phosphoramide chloridate (0.58 g, 0.95 mmol), and the mixture was stirred at room temperature for 19 hours. N,N-diisopropylethylamine (1.38 mL, 7.93 mmol), prolylglutamic acid (0.39 g, 1.59 mmol) and 2,2,2-trifluoroethanol (2.46 mL, 34.3 mmol) were added thereto, and the mixture was stirred at room temperature for 2 hours. The mixture was partition-washed with water (12.7 mL×2), and a lower layer containing TBSO-PMO[$C^{PhyTOB}$-T]-Tr was recovered. After ice-cooling, a chloroform solution (0.80 ml) of trifluoroacetic acid (0.16 g, 1.40 mmol) was added dropwise. The obtained solution was concentrated under reduced pressure, and subjected to the subsequent reaction.

TOF-MS+ (m/z) 1906.8

4) Deprotection of Trityl Group-2

The organic layer (12.1 mL) containing TBSO-PMO[$C^{PhyTOB}$-T]-Tr (1.21 g, corresponding to 0.63 mmol) was ice-cooled, and 2,2,2-trifluoroethanol (2.73 mL, 38.1 mmol) and thiomalic acid (0.29 g, 1.90 mmol) were added thereto. A chloroform solution (1.00 mL) of trifluoroacetic acid (0.58 g, 5.07 mmol) and triethylamine (0.32 g, 3.17 mmol) was added dropwise to the mixture, and the mixture was stirred at 15° C. for 1.5 hours. A chloroform solution (0.50 mL) of N,N-diisopropylethylamine (0.33 g, 2.54 mmol) was added dropwise. The mixture was successively partition-washed with a mixed solution (4:1, 18.1 mL×2) of 5% aqueous sodium carbonate and N,N-dimethylformamide and a mixed solution (3:2, 18.1 mL×3) of 20% brine and N,N-dimethylformamide, and a lower layer containing TBSO-PMO[$C^{PhyTOB}$-T]-H was recovered, concentrated under reduced pressure, and subjected to the subsequent reaction.

TOF-MS+ (m/z) 1664.5

5) Condensation-3

To the organic layer (10.6 mL) containing TBSO-PMO[$C^{PhyTOB}$-T]-H (1.06 g, corresponding to 0.63 mmol) were added N,N-diisopropylethylamine (0.20 mL, 1.14 mmol) and {2-(N-benzoyladenyl)-4-tritylmorpholin-6-yl}methyldimethyl phosphoramide chloridate (0.69 g, 0.95 mmol), and the mixture was stirred at room temperature for 68.5 hours. To the reaction mixture were added N,N-diisopropylethylamine (1.38 mL, 7.93 mmol), prolylglutamic acid (0.39 g, 1.59 mmol) and 2,2,2-trifluoroethanol (5.12 mL, 71.3 mmol), and the mixture was stirred at room temperature for 1 hour. The mixture was partition-washed with water (21.1 mL×2), and a lower layer containing TBSO-PMO[$C^{PhyTOB}$-T-$A^{bz}$]-Tr was recovered and concentrated under reduced pressure to give an oil containing the objective compound.

TOF-MS+ (m/z) 2350.2

INDUSTRIAL APPLICABILITY

According to the present invention, by performing a condensation reaction in the liquid phase, the reactivity is remarkably improved as compared to the solid-phase method, monomer equivalents to be used can be strikingly reduced, and morpholino oligonucleotide can be conveniently isolated and purified by an extraction operation after the reaction. Therefore, morpholino oligonucleotide having a chain length utilizable as a pharmaceutical product can be produced efficiently and in a high yield by a liquid-phase synthesis process.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A morpholino nucleotide represented by formula (I):

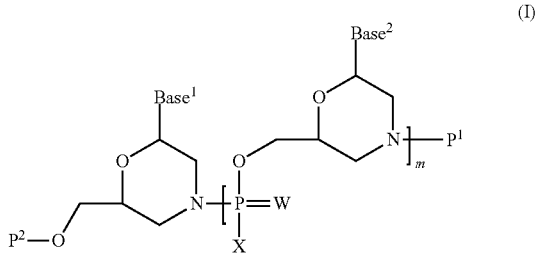

wherein
m is any integer of not less than 0,
$P^1$ is a hydrogen atom, or a temporary protecting group removable under acidic conditions,
$P^2$ is a protecting group having an alkyl group having not less than 10 and not more than 300 carbon atoms and/or an alkenyl group having not less than 10 and not more than 300 carbon atoms or a protecting group removable under conditions different from those for $P^1$,
Base$^1$ is a nucleic acid base optionally protected by a protecting group,
Base$^2$ in the number of m are each independently a nucleic acid base optionally protected by a protecting group,
each X in the number of m is independently a di $C_{1-6}$ alkylamino group, or a 1-piperazinyl group wherein a nitrogen atom at the 4-position is protected by a protecting group and further optionally substituted, and
W in the number of m are each an oxygen atom, provided that:
1) at least one of said protecting group when Base$^1$ is protected by a protecting group, any protecting group when any Base$^2$ in the number of m are protected by a protecting group, and a protecting group for $P^2$ is a protecting group having an alkyl group having not less than 10 and not more than 300 carbon atoms and/or an alkenyl group having not less than 10 and not more than 300 carbon atoms, and
2) when $P^2$ is a protecting group having a linear alkyl group having not less than 10 and not more than 300 carbon atoms and/or a linear alkenyl group having not less than 10 and not more than 300 carbon atoms, at least one of Base$^1$ and any Base$^2$ in the number of m is a nucleic acid base protected by a protecting group having an alkyl group having not less than 10 and not more than 300 carbon atoms and/or an alkenyl group having not less than 10 and not more than 300 carbon atoms.

2. The morpholino nucleotide according to claim 1, wherein m is an integer of 0 to 19.

3. The morpholino nucleotide according to claim 1, wherein the protecting group having an alkyl group having not less than 10 and not more than 300 carbon atoms and/or an alkenyl group having not less than 10 and not more than 300 carbon atoms is a group represented by formula (II):

wherein:
L is a single bond, or a group represented by formula (a1):

wherein:
\* indicates the bonding position to Y;
\*\* indicates the bonding position to an oxygen atom or a nitrogen atom to be protected;
$L_1$ is an optionally substituted divalent $C_{1-22}$ hydrocarbon group; and
$L_2$ is C(=O) or a group represented by \*\*\*N(R$^3$)—R$^1$—N(R$^2$)C(=O)\*\*, wherein \*\* indicates the bonding position to L$^1$, \*\*\* indicates the bonding position to Y, R$^1$ is an optionally substituted $C_{1-22}$ alkylene group, R$^2$ and R$^3$ are each independently a hydrogen atom or an optionally substituted $C_{1-22}$ alkyl group, or R$^2$ and R$^3$ are optionally joined to form an optionally substituted $C_{1-22}$ alkylene bond,
Y is a single bond, an oxygen atom or NR, wherein R is a hydrogen atom, an alkyl group or an aralkyl group, and
Z is a group represented by formula (a2):

wherein:
\* indicates the bonding position to Y;
ring A is a benzene ring or a cyclohexane ring;
R$^4$ is a hydrogen atom, or when R$_b$ is a group represented by the following formula (a3) and both ring A and ring B are benzene rings, R$^4$ is optionally a single bond or O— in combination with R$^6$ to form a fluorenyl group or a xanthenyl group together with ring B;
each Q in the number of k is independently a single bond, or —O—, —S—, —OC(=O)—, —NHC(=O)— or —NH—;
each R$^5$ in the number of k is independently an organic group having an alkyl group having not less than 10 and not more than 300 carbon atoms and/or an alkenyl group having not less than 10 and not more than 300 carbon atoms;
k is an integer of 1 to 4;

ring A optionally further has, in addition to $QR^5$ in the number of k, a substituent selected from the group consisting of a halogen atom, a $C_{1-6}$ alkyl group optionally substituted by a halogen atom(s), and a $C_{1-6}$ alkoxy group optionally substituted by a halogen atom(s);

$R_a$ is a hydrogen atom;

$R_b$ is a hydrogen atom, or a group represented by formula (a3):

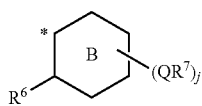

wherein:
* indicates a bonding position;
ring B is a benzene ring or a cyclohexane ring;
j is an integer of 0 to 4;
each Q in the number of j is as defined above;
each $R^7$ in the number of j is independently an organic group having an alkyl group having not less than 10 and not more than 300 carbon atoms and/or an alkenyl group having not less than 10 and not more than 300 carbon atoms;

$R^6$ is a hydrogen atom, or optionally a single bond or O— in combination with $R^4$ to form a fluorenyl group or a xanthenyl group together with ring A; and ring B optionally further has, in addition to $QR^7$ in the number of j, a substituent selected from the group consisting of a halogen atom, a $C_{1-6}$ alkyl group optionally substituted by a halogen atom(s), and a $C_{1-6}$ alkoxy group optionally substituted by a halogen atom(s)), or $R_a$ and $R_b$ are joined to form a carbonyl group.

4. The morpholino nucleotide according to claim 1, wherein the protecting group having an alkyl group having not less than 10 and not more than 300 carbon atoms and/or an alkenyl group having not less than 10 and not more than 300 carbon atoms is selected from the group consisting of a 3,4,5-tri(octadecyloxy)benzoyl group and a 3,4,5-tri(2',3'-dihydrophytyloxy)benzoyl group.

5. The morpholino nucleotide according to claim 1, wherein $P^2$ is a silyl protecting group.

6. The morpholino nucleotide according to claim 1, wherein $P^2$ is a tert-butyldimethylsilyl group, a diisopropylphenylsilyl group, a triphenylsilyl group, or a diphenyl tert-butoxysilyl group.

7. The morpholino nucleotide according to claim 1, wherein $P^1$ is a trityl group, a monomethoxytrityl group, or a dimethoxytrityl group.

* * * * *